US009309507B2

(12) United States Patent
Henry

(10) Patent No.: US 9,309,507 B2
(45) **Date of Patent: *Apr. 12, 2016**

(54) CONJUGATED BLOOD COAGULATION FACTOR VIIA

(75) Inventor: William Henry, Haddenham (GB)

(73) Assignee: Polytherics Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/643,504

(22) PCT Filed: Apr. 28, 2011

(86) PCT No.: PCT/GB2011/000663

§ 371 (c)(1), (2), (4) Date: Feb. 4, 2013

(87) PCT Pub. No.: WO2011/135308

PCT Pub. Date: Nov. 3, 2011

(65) Prior Publication Data

US 2013/0129698 A1 May 23, 2013

(30) Foreign Application Priority Data

Apr. 30, 2010 (GB) .................................. 1007356.7

(51) Int. Cl.

| | |
|---|---|
| ***A61K 38/00*** | (2006.01) |
| ***C12N 9/96*** | (2006.01) |
| ***A61K 47/48*** | (2006.01) |
| ***A61K 38/48*** | (2006.01) |
| ***A61K 45/00*** | (2006.01) |

(52) U.S. Cl.

CPC .............. *C12N 9/96* (2013.01); *A61K 38/4846* (2013.01); *A61K 45/00* (2013.01); *A61K 47/48215* (2013.01)

(58) Field of Classification Search

CPC .. A61K 38/37; A61K 38/4846; A61K 49/085

See application file for complete search history.

(56) References Cited

U.S. PATENT DOCUMENTS

| | | | | |
|---|---|---|---|---|
| 5,925,739 | A | 7/1999 | Spira et al. | |
| 5,972,885 | A | 10/1999 | Spira et al. | |
| 6,806,063 | B2 | 10/2004 | Pedersen et al. | |
| 7,199,223 | B2 | 4/2007 | Bossard et al. | |
| 7,235,638 | B2 | 6/2007 | Persson | |
| 7,579,444 | B2 | 8/2009 | Bossard et al. | |
| 7,632,921 | B2 | 12/2009 | Pan et al. | |
| 7,683,158 | B2 | 3/2010 | Siekmann et al. | |
| 7,863,421 | B2 | 1/2011 | Bossard et al. | |
| 8,143,378 | B2 | 3/2012 | Bossard et al. | |
| 8,247,536 | B2 | 8/2012 | Bossard et al. | |
| 2006/0052302 | A1 * | 3/2006 | Bossard et al. | 514/12 |
| 2008/0188400 | A1 | 8/2008 | Ropke et al. | |
| 2008/0200651 | A1 | 8/2008 | Ostergaard et al. | |
| 2008/0221032 | A1 | 9/2008 | Turecek et al. | |
| 2009/0176967 | A1 | 7/2009 | Stennicke | |
| 2009/0227504 | A1 | 9/2009 | Klausen et al. | |
| 2010/0028939 | A1 | 2/2010 | Behrens et al. | |
| 2010/0056428 | A1 | 3/2010 | Behrens | |
| 2010/0093934 | A1 | 4/2010 | Mitterer et al. | |
| 2010/0099616 | A1 | 4/2010 | Turecek et al. | |
| 2010/0249033 | A1 | 9/2010 | Bossard et al. | |

FOREIGN PATENT DOCUMENTS

| | | | |
|---|---|---|---|
| WO | WO-9501804 | A1 | 1/1995 |
| WO | WO-9511924 | A1 | 5/1995 |
| WO | WO-9711957 | A1 | 4/1997 |
| WO | WO-9832466 | A1 | 7/1998 |
| WO | WO-02077218 | A1 | 10/2002 |
| WO | WO-03092602 | A2 | 11/2003 |
| WO | WO-2004030617 | A2 | 4/2004 |
| WO | WO-2004060965 | A2 | 7/2004 |
| WO | WO-2004075923 | A2 | 9/2004 |
| WO | WO-2005007197 | A2 | 1/2005 |
| WO | WO-2006053299 | A2 | 5/2006 |
| WO | WO-2007126808 | A1 | 11/2007 |
| WO | WO-2008098930 | A1 | 8/2008 |
| WO | WO-2008127702 | A2 | 10/2008 |
| WO | WO-2009047500 | A1 | 4/2009 |
| WO | WO-2009130602 | A2 | 10/2009 |
| WO | WO-2010010324 | A1 | 1/2010 |
| WO | WO-2010033207 | A1 | 3/2010 |
| WO | WO-2010033218 | A1 | 3/2010 |
| WO | WO-2010033223 | A1 | 3/2010 |
| WO | WO-2010033240 | A2 | 3/2010 |
| WO | WO-2010045568 | A1 | 4/2010 |
| WO | WO-2010062768 | A1 | 6/2010 |
| WO | WO-2010070300 | A2 | 6/2010 |
| WO | WO-2010083536 | A1 | 7/2010 |
| WO | WO-2011007148 | A1 | 1/2011 |

(Continued)

OTHER PUBLICATIONS

Johansen et al., Thromb Haemost, 2010; 104: 157-164, available online: Apr. 13, 2010.*

Balan et al., Bioconjugate Chem. 2007, 18, 61-76.*

Brocchini, Steve et al. "PEGylation of Native Disulfide Bonds in Proteins." Nature Protocols. vol. 1, No. 5. Dec. 14, 2006. 12 pages.

International Search Report for International Patent Application No. PCT/GB2011/000663 mailed Jul. 1, 2011. 5 pages.

Shaunak, Sunil et al. "Site-specific PEGylation of Native Disulfide Bonds in Therapeutic Proteins." Nature Chemical Biology. vol. 2, No. 6. Jun. 2006. 13 pages.

(Continued)

*Primary Examiner* — Thomas S Heard

*Assistant Examiner* — Kaipeen Yang

(74) *Attorney, Agent, or Firm* — Wilmer Cutler Pickering Hale and Dorr LLP

(57) ABSTRACT

The present invention provides a biocompatible polymer conjugated to FVIIa via one or more cysteine residues, suitably via a linker across a reduced disulphide bond in FVIIa, and pharmaceutical compositions comprising such conjugated forms of FVIIa.

25 Claims, 15 Drawing Sheets

(56) References Cited

FOREIGN PATENT DOCUMENTS

| | | | |
|---|---|---|---|
| WO | WO-2011101242 | A1 | 8/2011 |
| WO | WO-2011103531 | A1 | 8/2011 |

OTHER PUBLICATIONS

Bjoern, Soeren et al. "Human Plasma and Recombinant Factor VII." The Journal of Biological Chemistry. vol. 266, No. 17, Jun. 15, 1991. pp. 11051-11057. 7 pages.

Nishimura, Hitoshi et al. "Identification of a Disaccharide (Xyl-Glc) and a Trisaccharide ($Xyl_2$- Glc) *O*-Glycosidically Linked to a Serine Residue in the First Epidermal Growth Factor-like Domain of Human Factors VII and IX and Protein Z and Bovine Protein Z." The Journal of Biological Chemistry. vol. 264, No. 34. Dec. 5, 1989. pp. 20320-20325. 6 pages.

Plesner, Bitten et al. "Biophysical Characterisation of GlycoPEGylated Recombinant Human Factor VIIa." International Journal of Pharmaceutics. 406, Jan. 12, 2011. pp. 62-68. 7 pages.

PR Newswire; Pro Bono Bio Announces the Successful Development of Subcutaneous and Long-Acting Blood Factors VIIa, VIII and IX for the Treatment of Haemophilia; Sep. 11, 2012, 4 pages. Source by Sys.con Media.

Zloh, Mire et al. "Identification and Insertion of 3-carbon Bridgesin Protein Disulfide Bonds: A Computational Approach." *Nature Protocols*. vol. 2, No. 5. Apr. 26, 2007. pp. 1070-1083.

* cited by examiner

CONJUGATED BLOOD COAGULATION FACTOR VIIA

The present invention relates to conjugated forms of the human blood coagulation Factor VIIa.

Blood coagulation Factor VII (herein referred to as FVII) is a 53,000 Dalton (Da), glycosylated, Vitamin K dependent, single-chain zymogen, containing 12 native disulphide bonds (O'Hara et al., *Proc. Nat'l Acad. Sci. USA,* 84: 5158-5162 (1987)). The protein is predominantly produced in the liver. FVII is involved in the extrinsic blood clotting cascade (FIG. 1). The protein is organised into four discrete domains: an N-terminal γ-carboxyglutamate (Gla) domain, two epidermal growth factor-like (EGF) domains and a C-terminal serine protease domain. The circulating zymogen shows very little protease activity in the absence of its cofactor tissue factor (TF) which is found in the vascular subendothelium. Following vascular damage, FVII binds to TF with high affinity and is converted to the active, two-chain enzyme FVIIa by specific cleavage of the peptide bond between arginine 152 and isoleucine 153. The FVIIa light-chain is composed of the N-terminal Gla and EGF-like domains and the heavy-chain is composed of the serine protease domain. The heavy and light chains are held together by a single disulphide bond between cysteine 135 and cysteine 262. Once activated, FVIIa rapidly catalyses the conversion of FX to FXa and FIX to FIXa. FXa then forms a complex with FVa to cleave prothrombin, resulting in the generation of small amounts of thrombin (Aitken, M. G. *EMA,* 16: 446-455 (2004)). This thrombin generation activates platelets and cofactors V, VIII and XI on the platelet surface. The activation leads to the formation of a thrombin burst which causes fibrin polymerisation and the formation of a haemostatic plug.

Human recombinant FVIIa has been developed and commercialised by Novo Nordisk as NovoSeven® (eptacog alfa [activated], ATC code B02BD08). NovoSeven® is licensed for the treatment of bleeding episodes in haemophilia A or B patients who have developed inhibitory antibodies against FVIII or IX, respectively (Jurlander et al., *Seminars in Thrombosis and Hemostasis,* 27: 373-383 (2001); Roberts et al., *Blood,* 15: 3858-3864 (2004)). The treatment has proved to be safe and effective since its launch in 1996. However, due to the proteins relatively short in vivo half-life (2.3 hours; Summary Basis for Approval NovoSeven®, FDA reference number 96-0597) multiple infusions of high doses of the product (90 μg $kg^{-1}$) are required over time during a single bleeding episode in order to attain haemostasis. The short half-life of the product and the high dose required to render the desired therapeutic effect preclude the common use of NovoSeven® for prophylactic treatment of haemophiliacs with inhibitors. Clearly, therefore, there is a need for the development of FVIIa molecules which have an increased half-life, producing improvements in pharmacokinetics (PK) and pharmacodynamics (PD).

The conjugation of biopharmaceuticals to biocompatible polymers has previously been used successfully to improve the physicochemical characteristics of products. Characteristics of therapeutic proteins which have been improved through conjugation include PK, PD and immunogenicity. The attachment of a chemical moiety to a protein can significantly increase its circulation half-life (Jevsevar et al., *Biotechnol. J.,* 5: 113-128 (2010)). For molecular species with molecular weights below the glomerular filtration limit the conjugation of a large molecular weight moiety prevents renal clearance of the product. Also, addition of chemical moieties to pharmaceutical products can prevent receptor mediated removal of the molecule through steric hindrance.

An example of a biocompatible polymer which has been used in several marketed biopharmaceutical products is polyethylene glycol (herein referred to as PEG). The process of covalently attaching a PEG molecule to another molecule is termed PEGylation. To date, nine PEGylated products have received FDA market approval, with four being blockbuster drugs: PegIntron® (Schering-Plough), Pegasys® (Hoffman-La Roche), Neulasta® (Amgen) and Micera® (Hoffman-La Roche). A number of different chemistries have been used to conjugate protein therapeutics to activated PEG molecules. Random PEGylation has been used successfully to covalently link PEG moieties to proteins through amino groups on proteins. The attachment sites have most frequently, but not exclusively, been the ϵ-amino group on the side chains of lysine residues. Such random reactions can produce very complex mixtures of conjugates varying in the number and site of PEG moiety attachment. Even following purification of random conjugation reactions, positional isomers can be present which demonstrate very different physicochemical and pharmaceutical characteristics. A number of site-specific PEGylation techniques have been developed and are now being exploited to produce better defined biopharmaceuticals. Approaches taken to render site-specific PEGylation include N-terminal, cysteine, glycan, disulphide and polyhistidine targeted PEGylation.

The state of the art in PEGylation of recombinant FVIIa is documented by different patents and patent applications:

WO 98/32466 suggests that FVII may be PEGylated, but does not contain any further information on the subject.

US 2008/0200651 suggests that FVII polypeptides with wild-type, or increased, activity which have a PEG molecule conjugated via an artificially introduced cysteine residue demonstrate increased in vivo half-life.

US 2008/0221032 describes the production of a FVIIa-polysialic acid conjugate which resulted in the molecule demonstrating a significantly increased in vivo half-life.

US 2009/0176967 teaches that enzymes can be used to introduce specific functional groups at the C-terminus of the FVII polypeptide to which biocompatible polymers such as PEG can be coupled.

US 2009/0227504 describes preparations of FVIIa (or FVIIa-like molecules) where one, or more, asparagine—and/or serine-linked oligosaccharide chains are covalently modified with at lease one polymeric group which demonstrate improved serum half-life.

US 2010/0028939 describes how natural glycoproteins can be modified using the enzyme galactose oxidase to produce reactive aldehyde functionalities on the glycan termini. The reactive aldehydes can then be used to conjugate polymeric moieties to the protein producing a product with improved pharmacological characteristics.

US 2010/0056428 suggests that improved pharmacokinetic characteristics can be achieved in FVIIa by the derivatisation of the glycoprotein by an oxime of a polymeric moiety such as PEG at a glycosyl group.

US 2010/0093934 teaches that the conjugation of polymeric moieties onto blood clotting factors can be somewhat targeted by first binding the coagulation factor to a monoclonal antibody, or antibodies, having affinity for the protein before reacting it with an activated polymer.

US 2010/0099616 describes how blood factors, including FVIIa can be manufactured with low numbers (1-9) of water soluble polymers conjugated to them. However, the authors do not exemplify the pharmacological characteristics of the PEGylated-FVIIa produced by this method.

Another approach to PEGylation of proteins has been developed by Polytherics and is known as TheraPEG™ in which a PEG polymer is attached to the protein of interest via a reduced disulphide bond of a pair of cysteine residues in the protein (WO 2005/007197). The technique has been used to prepare a PEGylated version of Factor IX free of contamination from Factor FIXa (WO 2009/130602).

However, with regard to using this same technology for the PEGylation of FVIIa, it was not considered to be trivial or routine.

Whilst proteins in the blood coagulation system may share a common purpose in terms of haemostasis, they all work very differently to the point that it would be unreasonable to assume that TheraPEG™ technology would provide an obvious route to improve the half-life and immunogenic profile of all of them. The differences are summarised thus:

From the point of view of activity of FVIIa with respect to FIX, certain key differences exist which means that conjugation of the protein with a biocompatible polymer is not a straightforward step to take.

For example, while FIX and FIXa, are involved in the intrinsic coagulation cascade, FVIIa participates principally in the extrinsic cascade. FIX once activated needs only to form an association with its cofactor, FVIII, to participate in the coagulation cascade. In contrast, FVIIa will only provoke coagulation in the presence of tissue factor (Tf), so for FVIIa to be active in coagulation it must have the ability to bind to Tf and also have its active site available to carry out peptide cleavage. The theoretical PEGylation of FVIIa using TheraPEG™ was thought likely to affect the ability of the protein to bind Tf and sterically hinder the active site. Other differences in terms of biological activity are that FIXa is inherently immunogenic but FVIIa is not.

FVIIa also can provoke coagulation by interacting directly with activated platelets. This particular process is less well understood but could involve a further receptor site association. To this effect FVIIa could in principal require three sites of interaction with its target ligands, all of which could be disrupted by PEGylation. Therefore, PEGylation of factor VIIa presents several unique and different challenges which are distinct and different to that of FIX.

Nevertheless, there remains a need for improved FVIIa molecules having biocompatible polymers conjugated to the polypeptide in a site-specific manner to extend the half-life of FVIIa in vivo, while retaining functional activity, as compared to unmodified FVIIa or other modified FVIIa therapeutics known in the art.

It has been discovered that the pharmacological properties of recombinant FVIIa may be enhanced by conjugating FVIIa to one or more biocompatible polymers. The enhanced pharmacological properties include an increase of in vivo circulating half-life when compared to unconjugated FVIIa.

According to a first aspect of the invention there is provided a biocompatible polymer conjugated to FVIIa via one or more cysteine residues.

The biocompatible polymer may be selected from the group consisting of polyethylene glycol (PEG), poly-phosphatidyl choline (PC), polypropylene glycol (PPG), copolymers of ethylene glycol and propylene glycol, polyethylene oxide (PEO), polyoxyethylated polyol, polyolefinic alcohol, polyhydroxyalkylmethacrylate, polysaccharides, poly α-hydroxy acid, polyvinyl alcohol, polyphosphosphasphazene, poly N-acryloylmorpholine, polyalkyene oxide polymers, polymaleic acid, poly DL-alanine, carboxymethylcellulose, dextran, starch or starch derivatives, hyaluronic acid chitin, polymethacrylates, polysialic acid (PSA), polyhydroxy alkanoates, poly amino acids and combinations thereof. The biocompatible polymer may have a linear or branched structure.

In a further embodiment, the biocompatible polymer is a protein selected from, but not limited to, the group consisting of FVII, albumin, transferrin, immunoglobulins including monoclonal antibodies, antibody fragments for example; single-domain antibodies, $V_L$, $V_H$, Fab, $F(ab')_2$, Fab', Fab3, scFv, di-scFv, sdAb, Fc and combinations thereof.

One or more biocompatible polymers may be conjugated to each FVIIa molecule if desired via one or more cysteine residues. A free cysteine residue is the result of reducing a cystine disulphide bond. The biocompatible polymer of the invention may be conjugated to FVIIa via one or more reduced cysteine disulphide bonds. The conjugation may be by means of a linker group bridging the sulphur residues of two cysteine residues that formed a disulphide bond in FVIIa. The disulphide bond may therefore be a native disulphide bond or a recombinantly introduced disulphide bond.

Where the biocompatible polymer is a PEG molecule it may be of any suitable molecular weight, for example from 5 to 100 kDa, 10 to 500 kDa, suitably 5 to 30 kDa or 10 to 30 kDa. Some suitable molecular weights include 10, 20, or 30 kDa.

There are several different types of polyethylene glycol polymers that will form conjugates with FVIIa. There are linear PEG polymers that contain a single polyethylene glycol chain, and there are branched or multi-arm PEG polymers. Branched polyethylene glycol contains 2 or more separate linear PEG chains bound together through a unifying group. For example, two PEG polymers may be bound together by a lysine residue. One linear PEG chain is bound to the α-amino group, while the other PEG chain is bound to the ϵ-amino group. The remaining carboxyl group of the lysine core is left available for covalent attachment to a protein. Both linear and branched polyethylene glycol polymers are commercially available in a range of molecular weights.

In one aspect of the invention, a FVIIa-PEG conjugate contains one or more linear polyethylene glycol polymers bound to FVIIa, in which each PEG has a molecular weight between about 2 kDa to about 100 kDa. In another aspect of the invention, a FVIIa-PEG conjugate contains one or more linear polyethylene glycol polymers bound to FVIIa, wherein each linear PEG has a molecular weight between about 5 kDa to about 40 kDa. In certain embodiments, each linear PEG has a molecular weight between about 10 kDa to about 30 kDa. In certain embodiments, each linear PEG has a molecular weight that is about 20 kDa. In certain embodiments, each linear PEG has a molecular weight that is less than about 10 kDa. In particular embodiments, where the FVIIa-PEG conjugate contains more than one linear PEG polymers bound to FVIIa, for example two, three, or up to eight linear PEG polymers bound to FVIIa. In some embodiments, the FVIIa-PEG conjugates contain multiple linear PEG polymers, where each linear PEG has a molecular weight of about 10-30 kDa.

A FVIIa-PEG conjugate of this invention may contain one or more branched PEG polymers bound to FVIIa, wherein each branched PEG has a molecular weight between about 2 kDa to about 100 kDa. In another aspect of the invention, a FVIIa-PEG conjugate contains one or more branched polyethylene glycol polymers bound to FVIIa, wherein each branched PEG has a molecular weight between about 5 kDa to about 40 kDa. In certain embodiments, each branched PEG has a molecular weight between about 5 kDa to about 30 kDa. In certain embodiments, each branched PEG has a molecular weight that is about 20 kDa. In certain embodiments, each branched PEG has a molecular weight that is less than about 10 kDa. In particular embodiments, where the FVIIa-PEG conjugate contains more than one branched PEG polymers bound to FVIIa, for example two, three, or up to eight branched PEG polymers bound to FVIIa. In a some embodiments, the FVIIa-PEG conjugates contains up to eight branched PEG polymers, where each branched PEG has a molecular weight of about 10-30 kDa.

The FVIIa-PEG conjugates may be purified by chromatographic methods known in the art, including, but not limited to ion exchange chromatography and size exclusion chromatography, affinity chromatography, precipitation and membrane-based separations.

Suitably, the biocompatible polymer moiety of the FVIIa conjugate may be bound to two cysteine residues, which form a disulphide bond in FVIIa. Therefore, the PEG containing linker bridges the disulphide bond. Examples of such conjugation procedures are described in WO 2005/007197, WO 2009/047500 and WO 2010/010324.

In one embodiment of the invention, a biocompatible polymer can be conjugated to FVIIa according to the scheme set out in FIG. 2. In FIG. 2, a group R1 is shown between the biocompatible polymer and the linker group spanning the sulphur atoms of the disulphide bond on the FVIIa molecule.

R1 represents a substituent which can be a direct bond, an alkylene group (preferably a $C_{1-10}$ alkylene group), or an optionally-substituted aryl or heteroaryl group; wherein the aryl groups include phenyl, benzoyl and naphthyl groups; wherein suitable heteroaryl groups include pyridine, pyrrole, furan, pyran, imidazole, pyrazole, oxazole, pyridazine, pyrimidine and purine; wherein linkage to the polymer may be by way of a hydrolytically labile bond, or by a nonlabile bond.

Particular substituents which may be present on the optionally substituted aryl or heteroaryl group include for example one or more of the same or different substituents selected from —CN, —$NO_2$, —$CO_2$R, —COH, —$CH_2$OH, —COR, —OR, —OCOR, —$OCO_2$R, —SR, —SOR, —$SO_2$R, —NHCOR, —NRCOR, —$NHCO_2$R, —NR'$CO_2$R, —NO, —NHOH, —NR'OH, —C═N—NHCOR, —C═N—NR'COR, —$N^+R_3$, —$N^+H_3$, —$N^+HR_2$, —$N^+H_2$R, halogen, for example fluorine or chlorine, —C≡CR, —C═$CR_2$ and $^{13}$C═CHR, in which each R or R' independently represents a hydrogen atom or an alkyl (preferably $C_{1-6}$) or an aryl (preferably phenyl) group. The presence of electron withdrawing substituents is especially preferred. In one embodiment, the optionally-substituted aryl or heteroaryl group in R1 includes aryl or heteroaryl groups substituted by an amide (NHCO) group which connects the R1 unit to the biocompatible polymer.

The linker group between the two sulphur atoms of the original disulphide bond between the cysteine residues of FVIIa may therefore comprise a 3-carbon bridge. In one embodiment, the linker group between the two sulphur atoms of the original disulphide bond between the cysteine residues of FVIIa is $(CH_2)_2$CHC(O)—.

In one embodiment of the invention, the biocompatible polymer may be conjugated as described above wherein the composition comprising FVIIa conjugated to a biocompatible polymer has the structure:

FVIIa / S / S / O / $R^1$-Biocompatible Polymer

In the broadest sense of the invention, the reagent may be represented as:

L / O / $R^1$-Biocompatible Polymer

Where R1 is as defined above and L is a leaving group.

L may represent —SR, —$SO_2$R, —$OSO_2$R, —$N^+R_3$, —$N^+HR_2$, —$N^+H_2$R, halogen (for example, fluorine or chlorine), or —OW, in which each R independently represents a hydrogen atom or an alkyl (for example $C_1$-$C_6$ alkyl) or aryl group (for example phenyl) and W represents a substituted aryl group (for example phenyl) containing at least one electron withdrawing substituent, for example one or more of the same or different substituents selected from —CN, —$NO_2$, —$CO_2$R, —COH, —$CH_2$OH, —COR, —OR, —OCOR, —$OCO_2$R, —SR, —SOR, —$SO_2$R, —NHCOR, —NRCOR, —$NHCO_2$R, —NR'$CO_2$R, —NO, —NHOH, —NR'OH, —C═N—NHCOR, —C═N—NR'COR, —$N^+R_3$, —$N^+H_3$, —$N^+HR_2$, —$N^+H_2$R, halogen, for example fluorine or chlorine, —C≡CR, —C═$CR_2$ and $^{13}$C═CHR, in which each R or R' independently represents a hydrogen atom or an alkyl (preferably $C_{1-6}$).

In one embodiment, where the leaving group L is $SO_2R^2$, in which each R2 independently represents a hydrogen atom or an alkyl (for example $C_1$-$C_6$ alkyl) or aryl group (for example phenyl), and R1 is as defined above, the conjugation reagent may have the formula $SO_2R^2$ / O / $R^1$-Biocompatible Polymer In one embodiment, the biocompatible polymer may be PEG and the leaving group may be —$SO_2R^2$, with R1 and R2 defined as above, the reagent is as follows:

$SO_2R^2$ / O / $R^1$—PEG

In another embodiment of the invention, the conjugation reagent may be formed from a specific arrangement in which the biocompatible polymer is connected via an amide moiety (CONH), where L is a leaving group as defined above. In other words, R1 is R3-CONH and the reagent has the following formula:

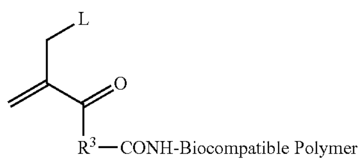

R3 represents a substituent which can be a direct bond, an alkylene group (preferably a $C_{1-10}$ alkylene group), or an optionally-substituted aryl or heteroaryl group; wherein the aryl groups include phenyl, benzoyl and naphthyl groups; wherein suitable heteroaryl groups include pyridine, pyrrole, furan, pyran, imidazole, pyrazole, oxazole, pyridazine, pyrimidine and purine; wherein linkage to the polymer may be by way of a hydrolytically labile bond, or by a nonlabile bond.

Particular substituents which may be present on the optionally substituted aryl or heteroaryl group include for example one or more of the same or different substituents selected from —CN, —$NO_2$, —$CO_2R$, —COH, —$CH_2OH$, —COR, —OR, —OCOR, —$OCO_2R$, —SR, —SOR, —$SO_2R$, —NHCOR, —NRCOR, —$NHCO_2R$, —$NR'CO_2R$, —NO, —NHOH, —NR'OH, —C═N—NHCOR, —C═N—NR'COR, —$N^+R_3$, —$N^+H_3$, —$N^+HR_2$, —$N^+H_2R$, halogen, for example fluorine or chlorine, —C≡CR, —C═$CR_2$ and $^{13}$C═CHR, in which each R or R' independently represents a hydrogen atom or an alkyl (preferably $C_{1-6}$) or an aryl (preferably phenyl) group. The presence of electron withdrawing substituents is especially preferred.

In embodiments where the moiety CONH is present, R2 and R3 are as defined above, and where the leaving group L is —$SO_2R^2$ the reagent is as follows:

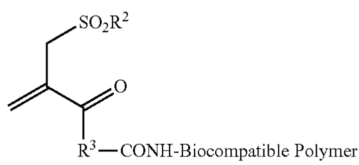

In such embodiments where the optionally-substituted aryl or heteroaryl group in R1 as defined above of the conjugation reagent includes aryl or heteroaryl groups substituted by an amide (NHCO) group, the structure of the conjugate protein, where R3 is as defined above, may be as follows:

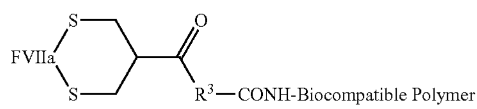

Where the biocompatible polymer is PEG, the conjugation reagent in this embodiment of the invention, where PEG is a polyethylene moiety and L is a leaving group, as defined above, is as follows:

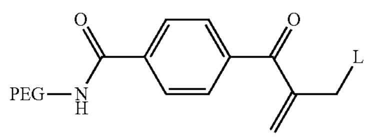

Where the reaction conditions are neutral or slightly basic then the following reagent may be used:

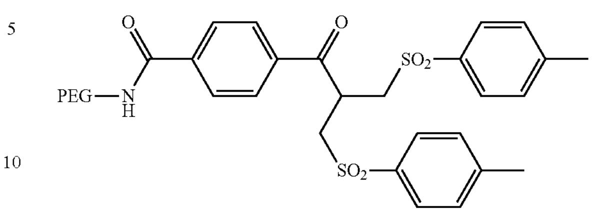

Under more acidic conditions, the above reagent may form the following molecule shown below, PEG mono-sulfone, which is also suitable for use in conjugation reactions as described herein.

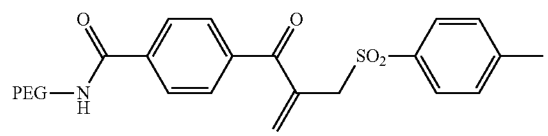

As used herein, the terms "Factor VIIa conjugate" or "FVIIa conjugate" refers to Factor VIIa that has been modified to include a biocompatible polymer moiety that results in an improved pharmacokinetic profile as compared to the unmodified Factor VIIa. The improvement in the pharmacokinetic profile may be observed as an improvement in one or more of the following parameters: activity, stability, area under the curve and circulating half-life.

The terms Factor VIIa (FVIIa) and Factor VII (FVII) are also used interchangeably unless the context specifies otherwise. In addition, the invention specifically includes conjugation of a biocompatible polymer to FVII, followed by subsequent activation of FVII to FVIIa.

The Factor VIIa may be from any suitable source. It may be produced using recombinant DNA technology, or it may be purified from blood plasma. It includes any active fragment or mutein thereof.

As used herein the term "muteins" refers to analogs of a FVIIa protein, in which one or more of the amino acid residues of the naturally occurring components of FVIIa are replaced by different amino acid residues, or are deleted, or one or more amino acid residues are added to the original sequence of an FVIIa, without changing considerably the activity of the resulting products as compared with the original FVIIa. These muteins are prepared by known synthesis and/or by site-directed mutagenesis techniques, or any other known technique suitable therefore.

Muteins in accordance with the present invention include proteins encoded by a nucleic acid, such as DNA or RNA, which hybridizes to DNA or RNA, which encodes an FVIIa, in accordance with the present invention, under stringent conditions. The term "stringent conditions" refers to hybridization and subsequent washing conditions, which those of ordinary skill in the art conventionally refer to as "stringent" (Ausubel et al., *Current Protocols in Molecular Biology*, Interscience, N.Y., sections 63 and 6.4 (1987, 1992); Sambrook et al. (Sambrook et al., *Molecular Cloning: A Laboratory Manual*, Cold Spring Harbor Laboratory Press, Cold Spring Harbor, N.Y. (1989)).

Without limitation, examples of stringent conditions include washing conditions 12-20° C. below the calculated Tm of the hybrid under study in, e.g., 2×SSC and 0.5% SDS for 5 minutes, 2×SSC and 0.1% SDS for 15 minutes; 0.1.times.SSC and 0.5% SDS at 37° C. for 30-60 minutes and then, a 0.1×SSC and 0.5% SDS at 68° C. for 30-60 minutes. Those of ordinary skill in this art understand that stringency conditions also depend on the length of the DNA sequences, oligonucleotide probes (such as 10-40 bases) or mixed oligonucleotide probes. If mixed probes are used, it is preferable to use tetramethyl ammonium chloride (TMAC) instead of SSC.

Any such mutein preferably has a sequence of amino acids sufficiently duplicative of that of an FVIIa, such as to have substantially similar, or even better, activity to FVIIa.

One characteristic activity of FVIIa is its capability of participate in the blood coagulation cascade and assays to detect FVIIa activity are described herein. As long as the mutein has substantial FVIIa activity, it can be considered to have substantially similar activity to FVIIa. Thus, it can be determined whether any given mutein has at least substantially the same activity as FVIIa by means of routine experimentation comprising subjecting such a mutein to assays as described herein.

In a preferred embodiment, any such mutein has at least 40% identity or homology with the amino acid sequence of FVIIa. More preferably, it has at least 50%, at least 60%, at least 70%, at least 80% or, most preferably, at least 90%, 95% or 99% identity or homology thereto.

Identity reflects a relationship between two or more polypeptide sequences or two or more polynucleotide sequences, determined by comparing the sequences. In general, identity refers to an exact nucleotide to nucleotide or amino acid to amino acid correspondence of the two polynucleotides or two polypeptide sequences, respectively, over the length of the sequences being compared.

For sequences where there is not an exact correspondence, a "percent identity" may be determined. In general, the two sequences to be compared are aligned to give a maximum correlation between the sequences. This may include inserting "gaps" in either one or both sequences, to enhance the degree of alignment. A percent identity may be determined over the whole length of each of the sequences being compared (so-called global alignment), that is particularly suitable for sequences of the same or very similar length, or over shorter, defined lengths (so-called local alignment), that is more suitable for sequences of unequal length.

Methods for comparing the identity and homology of two or more sequences are well known in the art. Thus for instance, programs available in the Wisconsin Sequence Analysis Package, version 9.1 (Devereux, et al., Nucleic acids Research, 12: 387 (1984)), for example the programs BESTFIT and GAP, may be used to determine the percentage identity between two polynucleotides and the percentage identity and the percentage homology between two polypeptide sequences. BESTFIT uses the "local homology" algorithm of Smith and Waterman (*Advances in Applied Mathematics,* 2; 482-489 (1981)) and finds the best single region of similarity between two sequences. Other programs for determining identity and/or similarity between sequences are also known in the art, for instance the BLAST family of programs (Atschul et al., *J. Molec. Biol.,* 215: 403 (1990), accessible through the home page of the NCBI at www.ncbi.nlm.nih.gov) and FASTA (Pearson W R, *Methods in Enzymology,* 183: 63-98 (1990)).

Muteins of FVIIa, which can be used in accordance with the present invention include a finite set of substantially corresponding sequences as substitution peptides which can be routinely obtained by one of ordinary skill in the art, without undue experimentation, based on the teachings and guidance presented herein.

Preferred changes for muteins in accordance with the present invention are what are known as "conservative" substitutions. Conservative amino acid substitutions of FVIIa may include synonymous amino acids within a group which have sufficiently similar physicochemical properties that substitution between members of the group will preserve the biological function of the molecule. It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues. Proteins and muteins produced by such deletions and/or insertions come within the scope of the present invention.

Thus the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains). Substitutions of this nature are often referred to as "conservative" or "semi-conservative" amino acid substitutions.

Amino acid changes relative to the sequence for the fusion protein of the invention can be made using any suitable technique e.g. by using site-directed mutagenesis.

It should be appreciated that amino acid substitutions or insertions within the scope of the present invention can be made using naturally occurring or non-naturally occurring amino acids. Whether or not natural or synthetic amino acids are used, it is preferred that only L-amino acids are present.

In addition fusion proteins comprising FVIIa and another peptide or protein fragment may be also be used provided that the fusion protein retains the activity of FVIIa. The term "fusion protein" in this text means, in general terms, one or more proteins joined together by chemical means, including hydrogen bonds or salt bridges, or by peptide bonds through protein synthesis or both.

"Functional derivatives" as used herein cover derivatives of FVIIa, and their muteins, which may be prepared from the functional groups which occur as side chains on the residues or are additions to the N- or C-terminal groups, by means known in the art, and are included in the invention as long as they remain pharmaceutically acceptable, i.e. they do not destroy the activity of the protein which is substantially similar to the activity of FVIIa, and do not confer toxic properties on compositions containing it.

These derivatives may, for example, include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carboxylic aroyl groups) or O-acyl derivatives of free hydroxyl groups (for example that of seryl or threonyl residues) formed with acyl moieties, including for example glycosylation of available hydroxyl residues.

An "active fragment of FVIIa" according to the present invention may be a fragment of FVIIa or a mutein as defined herein. The term fragment refers to any subset of the molecule, that is, a shorter peptide that retains the desired biological activity. Fragments may readily be prepared by removing amino acids from either end of the FVIIa molecule and testing the resultant fragment for its properties as described herein. Proteases for removing one amino acid at a time from either the N-terminal or the C-terminal of a polypeptide are known, and so determining fragments, which retain the desired biological activity, involves only routine experimentation.

As active fractions of an FVIIa, muteins and active fragments thereof, the present invention further covers any fragment or precursors of the polypeptide chain of the protein molecule alone or together with associated molecules or residues linked thereto, e.g., sugar or phosphate residues, or aggregates of the protein molecule or the sugar residues by themselves, provided said fraction has substantially similar activity to FVIIa.

The term “salts” herein refers to both salts of carboxyl groups and to acid addition salts of amino groups of the FVIIA molecule or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must retain the biological activity of FVIIa as described herein.

FVIIa conjugates may provide therapeutic benefits, for example, when compared to unconjugated FVIIa. Such therapeutic benefits include, but are not limited to, increased circulation half-life, reduced immunogenicity, higher activity, better stability, increased area under the curve, lower dosing requirements, and allowing for alternative routes of administration (e.g., subcutaneous).

Compared to unmodified FVIIa, the FVIIa conjugates of the invention may show an improvement in one or more parameters of the pharmacokinetic profile, including area under the curve (AUC), Cmax, clearance (CL), half-life, plasma residence time and bioavailability as compared to unmodified FVIIa.

The “area under the curve” or “AUC”, as used herein in the context of administering a peptide drug to a patient, is defined as total area under the curve that describes the concentration of drug in systemic circulation in the patient as a function of time from zero to infinity. As used herein the term “clearance” or “renal clearance” is defined as the volume of plasma that contains the amount of drug excreted per minute.

As used herein the term “half-life” or “t½”, in the context of administering a peptide drug to a patient, is defined as the time required for plasma concentration of a drug in a patient to be reduced by one half. There may be more than one half-life associated with the peptide drug depending on multiple clearance mechanisms, redistribution, and other mechanisms well known in the art. Usually, alpha and beta half-lives are defined such that the alpha phase is associated with redistribution, and the beta phase is associated with clearance. However, with protein drugs that are, for the most part, confined to the bloodstream, there can be at least two clearance half-lives. The precise impact of PEGylation on alpha phase and beta phase half-lives will vary depending upon the size and other parameters, as is well known in the art. Further explanation of “half-life” is found in Pharmaceutical Biotechnology (1997, DFA Crommelin and RD Sindelar, eds., Harwood Publishers, Amsterdam, pp 101-120).

As used herein the term “residence time”, in the context of administering a peptide drug to a patient, is defined as the average time that drug stays in the body of the patient after dosing.

As used herein the term “immunogenicity”, in the context of administering a peptide drug to a patient, is defined as the propensity of that drug to illicit an immune response in the patient after dosing, or after repeat dosing.

According to the present invention, the conjugation of FVIIa with a biocompatible polymer enhances the utility of FVIIa in pharmaceutical compositions. Moreover, the biocompatible moiety may protect FVIIa from degradation and antibody response. The FVIIa conjugates may have a prolonged circulating half-life, which results in a dose-sparing effect and less frequent administration.

As discussed above, PolyTherics has developed a technology, known as TheraPEG™ that can exploit the selective chemistry of naturally occurring sulphur atoms in proteins for site-specific PEGylation. The technology can also be applied to proteins and peptides where novel sulphur-containing groups have been introduced by recombinant or other means. PolyTherics has shown that disulphide bonds can be made more stable by the addition of a PEG-linked carbon bridge and that it is possible to make such a modification to disulphide bonds in proteins while retaining tertiary structure and maintaining protein function. This has made it possible for the first time to exploit the conjugating thiol selectivity of the two sulphur atoms that make up a disulphide bond to conjugate biocompatible polymers to a protein of interest site-specifically in either native or selectively engineered proteins. One example, of this approach is to use the technology to add PEG moieties to a FVIIa protein (or to “PEGylate” the FVIIa protein).

The disulphide-bridging conjugation reagent is a latently cross-conjugated system capable of undergoing interactive Michael and retro-Michael reactions. This enables the two free thiols generated by the reduction of a native disulphide group to re-anneal across a 3 carbon bridge that linked the two sulphur groups of the original disulphide bond (For example, see FIG. 2 for a schematic representation of the conjugation reaction to add a PEG moiety). The conjugation reagent may be described as a “PEGylation” reagent when it comprises PEG as the biocompatible polymer used to PEGylate the FVIIa protein.

Mechanistically, a conjugated double bond in the conjugation reagent is required to initiate a sequence of addition reactions. Once thiolate addition occurs, elimination of the remaining sulphinic acid moiety becomes possible. This generates another conjugated double bond for the addition of a second thiolate anion and the formation of a 3-carbon bridge between the two sulphur atoms. The end result is two very stable thiol-ether bonds either side of the carbon bridge.

The fact that PEGylation of FIX employing TheraPEG™ technology was successful is no guide to the success or otherwise of preparing PEGylated FVIIa using the same approach as it is a structurally and functionally different protein. It is highly surprising therefore that PEGylated FVIIa prepared using TheraPEG™ technology performs so well in in vivo experiments.

Moreover, the initial in vitro end-point coagulation assays carried out suggested that the above concerns regarding the multiple association requirements of FVIIa were well founded as the activity was low. It was only through the use of a different rate-based assay that gave the present inventors, surprisingly, confidence that the “standard” FVIIa activity assay was giving an underestimate of the activity and therefore the studies progressed to in vivo experiments.

According to a second aspect of the invention there is provided a pharmaceutical composition comprising a biocompatible polymer conjugated to FVIIa via one or more cysteine residues as defined in relation to the first aspect of the invention.

The pharmaceutical composition of the invention may further comprise a pharmaceutically acceptable diluent, adjuvant or carrier.

Pharmaceutical compositions adapted for oral administration may be presented as discrete units such as capsules, as solutions, syrups or suspensions (in aqueous or non-aqueous liquids; or as edible foams or whips; or as emulsions). Suitable excipients for tablets or hard gelatine capsules include lactose, maize starch or derivatives thereof, stearic acid or salts thereof. Suitable excipients for use with soft gelatine capsules include for example vegetable oils, waxes, fats, semi-solid, or liquid polyols etc. For the preparation of solutions and syrups, excipients which may be used include for example water, polyols and sugars. For the preparation of suspensions oils (e.g. vegetable oils) may be used to provide oil-in-water or water in oil suspensions.

Pharmaceutical compositions adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable compositions wherein the carrier is a liquid, for administration as a nasal spray or as nasal drops, include aqueous or oil solutions of the active ingredient. Pharmaceutical compositions adapted for administration by inhalation include fine particle dusts or mists which may be generated by means of various types of metered dose pressurised aerosols, nebulizers or insufflators.

Pharmaceutical compositions adapted for parenteral administration include aqueous and non-aqueous sterile injection solution which may contain anti-oxidants, buffers, bacteriostats and solutes which render the formulation substantially isotonic with the blood of the intended recipient; and aqueous and non-aqueous sterile suspensions which may include suspending agents and thickening agents. Excipients which may be used for injectable solutions include water, alcohols, polyols, glycerine and vegetable oils, for example. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets.

In general, the pharmaceutical compositions may contain preserving agents, solubilising agents, stabilising agents, wetting agents, emulsifiers, sweeteners, colourants, odourants, salts (substances of the present invention may themselves be provided in the form of a pharmaceutically acceptable salt), buffers, coating agents or antioxidants. They may also contain therapeutically active agents in addition to the substance of the present invention. The pharmaceutical compositions of the invention may be employed in combination with pharmaceutically acceptable diluents, adjuvants, or carriers. Such excipients may include, but are not limited to, saline, buffered saline (such as phosphate buffered saline), dextrose, liposomes, water, glycerol, ethanol and combinations thereof.

The pharmaceutical compositions may be administered in any effective, convenient manner effective for treating a patients disease including, for instance, administration by oral, intravenous, subcutaneous, intramuscular, intraosseous, intranasal, or routes among others. In therapy or as a prophylactic, the active agent may be administered to an individual as an injectable composition, for example as a sterile aqueous dispersion, preferably isotonic.

For administration to mammals, and particularly humans, it is expected that the daily dosage of the active agent will be from 0.01 mg/kg body weight, typically around 1 mg/kg. The physician in any event will determine the actual dosage which will be most suitable for an individual which will be dependent on factors including the age, weight, sex and response of the individual. The above dosages are exemplary of the average case. There can, of course, be instances where higher or lower dosages are merited, and such are within the scope of this invention.

Dosages of the substance of the present invention can vary between wide limits, depending upon the disease or disorder to be treated, the age and condition of the individual to be treated, etc. and a physician will ultimately determine appropriate dosages to be used.

This dosage may be repeated as often as appropriate. If side effects develop the amount and/or frequency of the dosage can be reduced, in accordance with normal clinical practice. In one embodiment, the pharmaceutical composition may be administered once every one to fourteen days.

According to a third aspect of the invention, there is provided a pharmaceutical composition of the second aspect and another pharmaceutically active agent. The other pharmaceutically active agent may promote or enhance the activity of FVIIa, for example another blood coagulation factor.

The pharmaceutical compositions of the invention may be employed alone or in conjunction with other compounds, such as therapeutic compounds or molecules, e.g. anti-inflammatory drugs, analgesics or antibiotics. Such administration with other compounds may be simultaneous, separate or sequential. The components may be prepared in the form of a kit which may comprise instructions as appropriate.

Preferably, the pharmaceutical composition of the invention and the other therapeutic compound are directly administered to a patient in need thereof.

The invention also provides a kit of parts comprising a pharmaceutical composition of invention, and an administration vehicle including, but not limited to, capsules for oral administration, inhalers for lung administration and injectable solutions for intravenous administration.

According to a fourth aspect of the invention, there is provided a method of treatment of a blood clotting disease or trauma where the method comprises administration of a composition of the present invention to a patient in need thereof. This aspect of the invention therefore also includes uses of such compositions in said methods.

Blood clotting diseases may be characterised by a loss of function of a blood clotting factor, or the generation of auto-antibodies. Examples of blood clotting diseases include haemophilia A and haemophilia B.

As used herein, the term "treatment" includes any regime that can benefit a human or a non-human animal. The treatment of "non-human animals" extends to the treatment of domestic animals, including horses and companion animals (e.g. cats and dogs) and farm/agricultural animals including members of the ovine, caprine, porcine, bovine and equine families. The treatment may be in respect of any existing condition or disorder, or may be prophylactic (preventive treatment). The treatment may be of an inherited or an acquired disease. The treatment may be of an acute or chronic condition.

According to a fifth aspect of the invention, there is provided a process for preparing the following conjugate of a biocompatible polymer and FVIIa as described above,

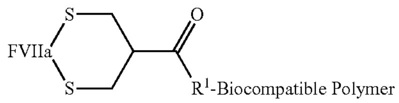

wherein the process comprises:

(a) reduction of a native disulphide bond between two cysteine residues in FVIIa, to generate two free thiol groups;
(b) a first thiolate addition reaction between a conjugation-reagent comprising a conjugated double bond and a leaving group;
(c) elimination of the leaving group, generating a conjugated double bond; and
(d) a second thiolate addition reaction, forming a 3-carbon bridge between the two sulphur atoms where R1 is as defined above.

In such a process, the conjugation reagent may have the formula, as described above, of:

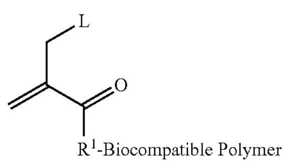

Where R1 is as defined above and L is a leaving group as defined above.

Further aspects of this embodiment of the invention are as described above in relation to the various structures of the conjugation reagent.

One example of a conjugation reagent which can be used, with substituents R1 and R2 as defined above, is as follows:

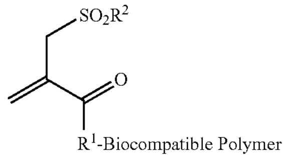

in which the leaving group is a sulfinyl group represented by $SO_2R^2$, as defined above.

Where the biocompatible polymer is PEG, the conjugation reagent can be as follows (as described above):

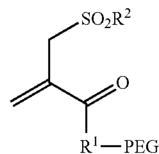

Preferred features for the second and subsequent aspects of the invention are as for the first aspect mutatis mutandis.

The present invention will now be further described with reference to the following Examples which are included for the purposes of reference and are not be construed as being limiting on the claimed invention.

In the present description and Examples reference is also made to a number of Figures in which:

FIG. 1 shows the blood coagulation cascade. Abbreviations: HMWK—High Molecular Weight Kininogen; PK—Prekallikrein; PL—Phospholipid.

Figure 4:
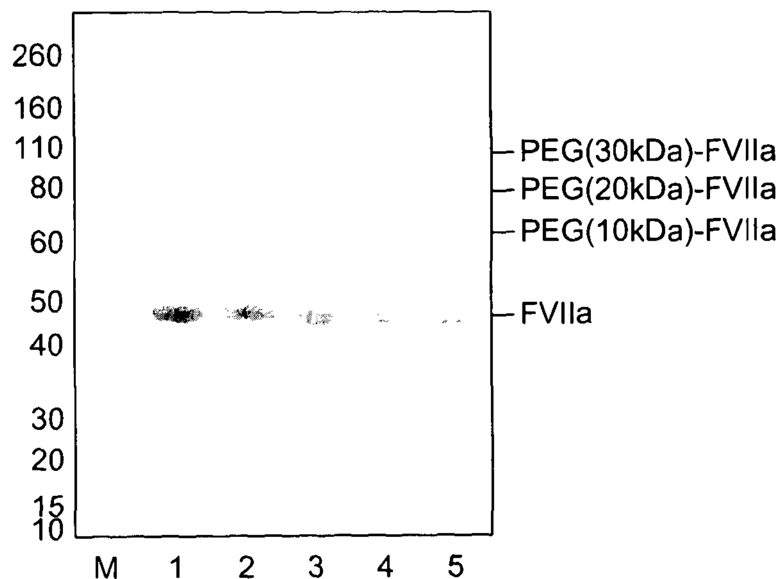

FIG. 4 shows Coomassie stain SDS-PAGE showing purified 10 kDa, 20 kDa and 30 kDa PEGylation reaction mixtures (lanes 3-5). FVIIa is shown in lane 1 and reduced FVIIa is shown in lane 2.

Figure 5:
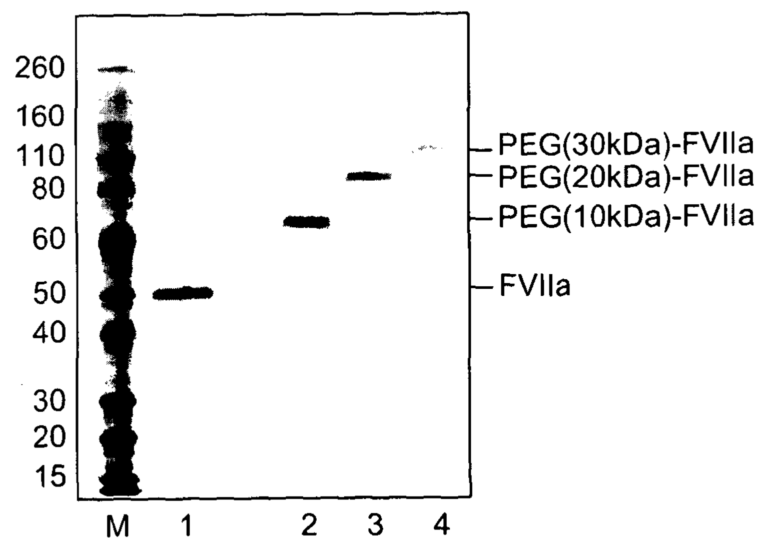

FIG. 5 shows silver stain SDS-PAGE showing purified 10 kDa, 20 kDa and 30 kDa mono-PEGylated FVIIa.

Figure 6:
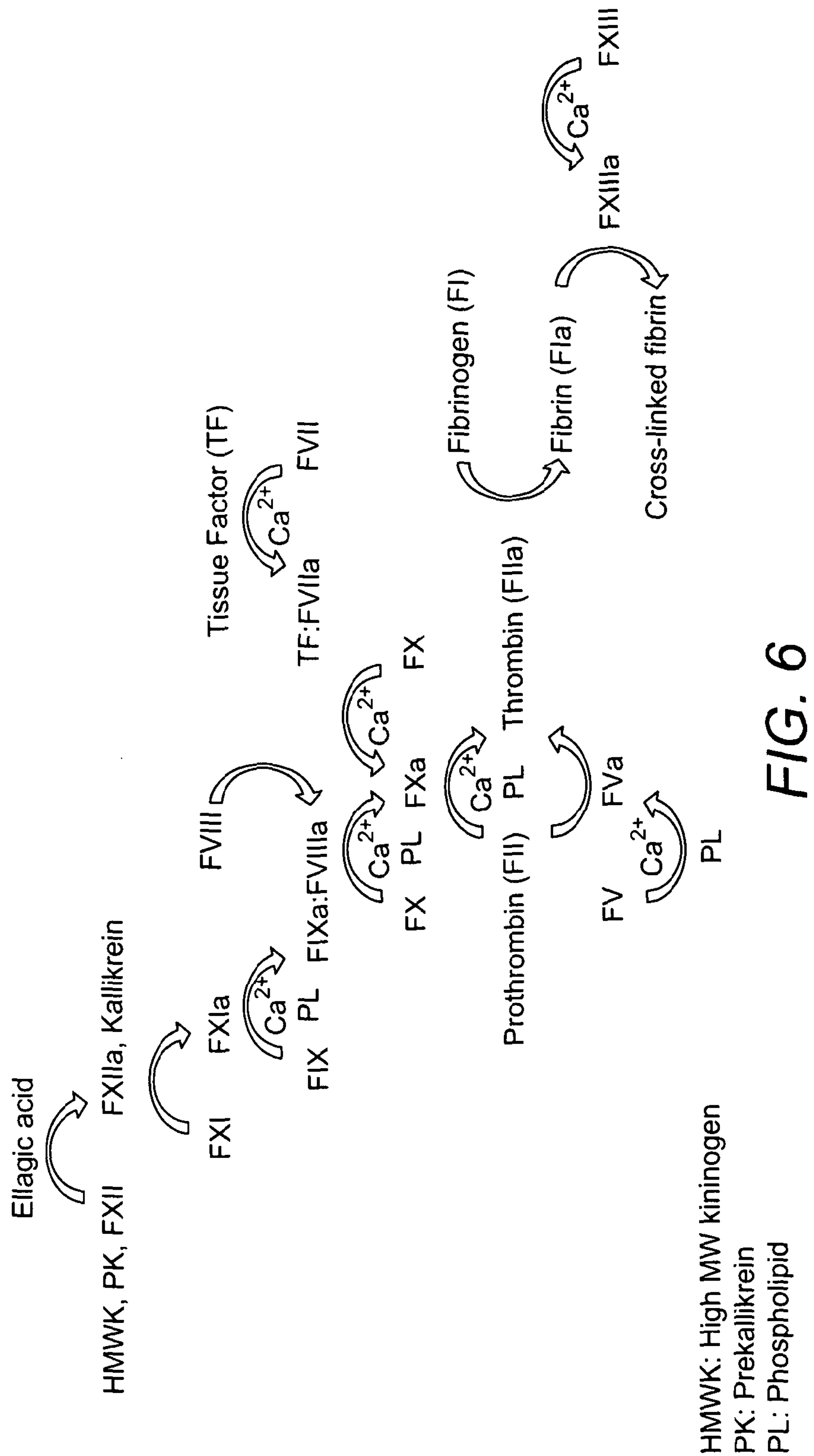

FIG. 6 shows a schematic diagram of the steps involved in a PT clotting assay. Arrows indicate thrombin-mediated amplification events. Abbreviations: HMWK—High Molecular Weight Kininogen; PK—Prekallikrein; PL-Phospholipid.

Figure 7:
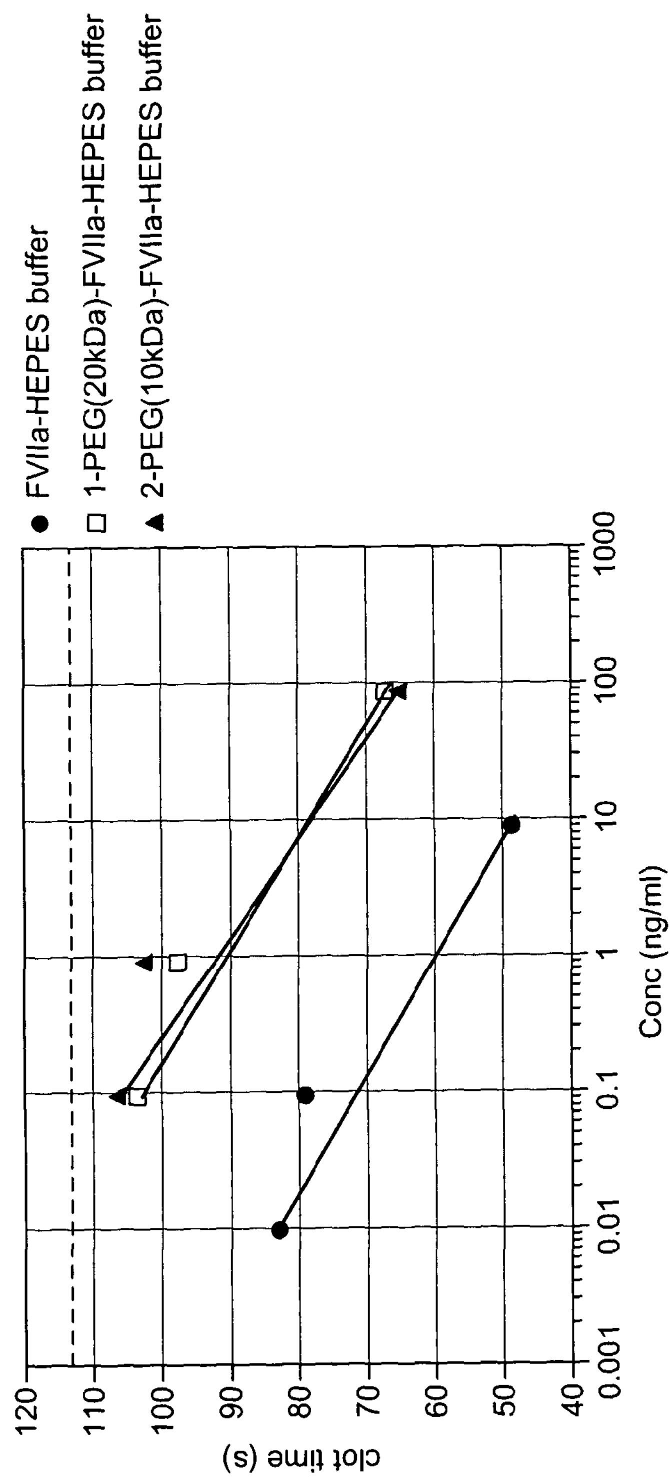

FIG. 7 shows concentration-dependent reduction in clotting times of PEGylated FVIIa (small-scale). Buffer (kit) clotted at 113 seconds.

Figure 8:
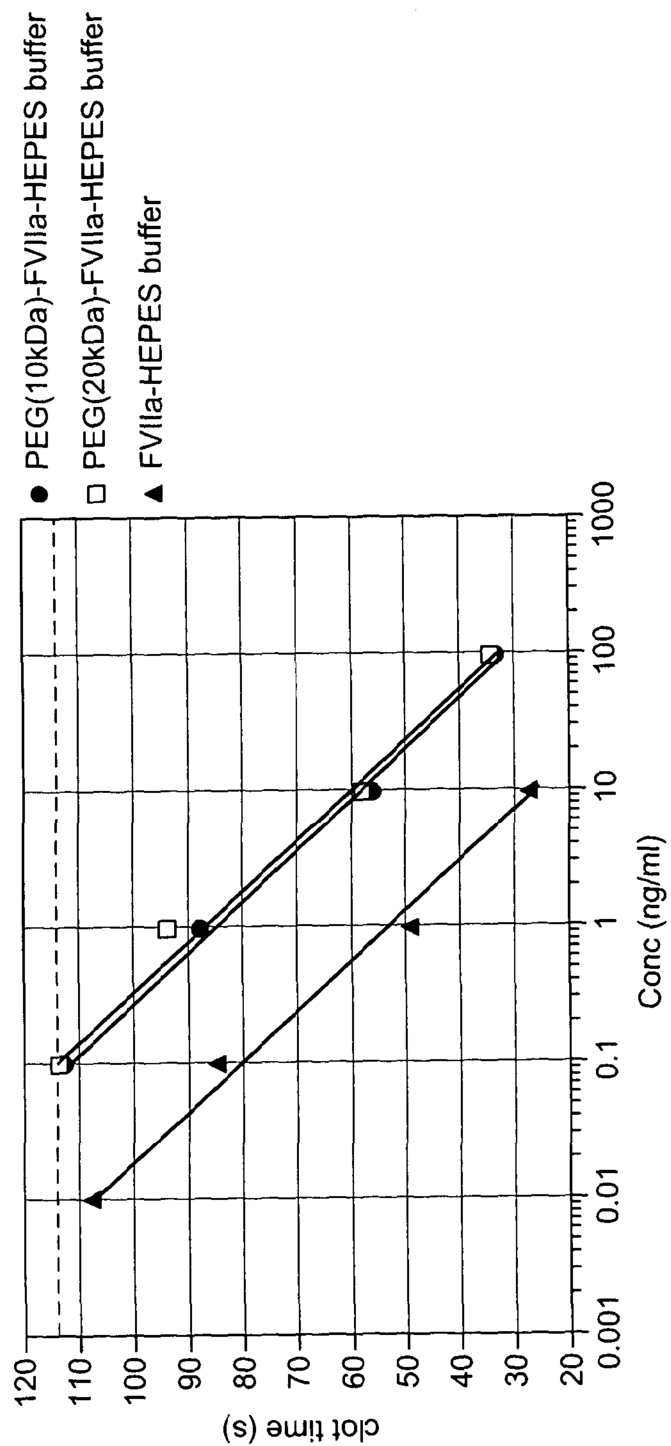

FIG. 8 shows concentration-dependent reduction in clotting times of PEGylated FVIIa (large-scale). Buffer (kit) clotted at 115 seconds.

Figure 9:
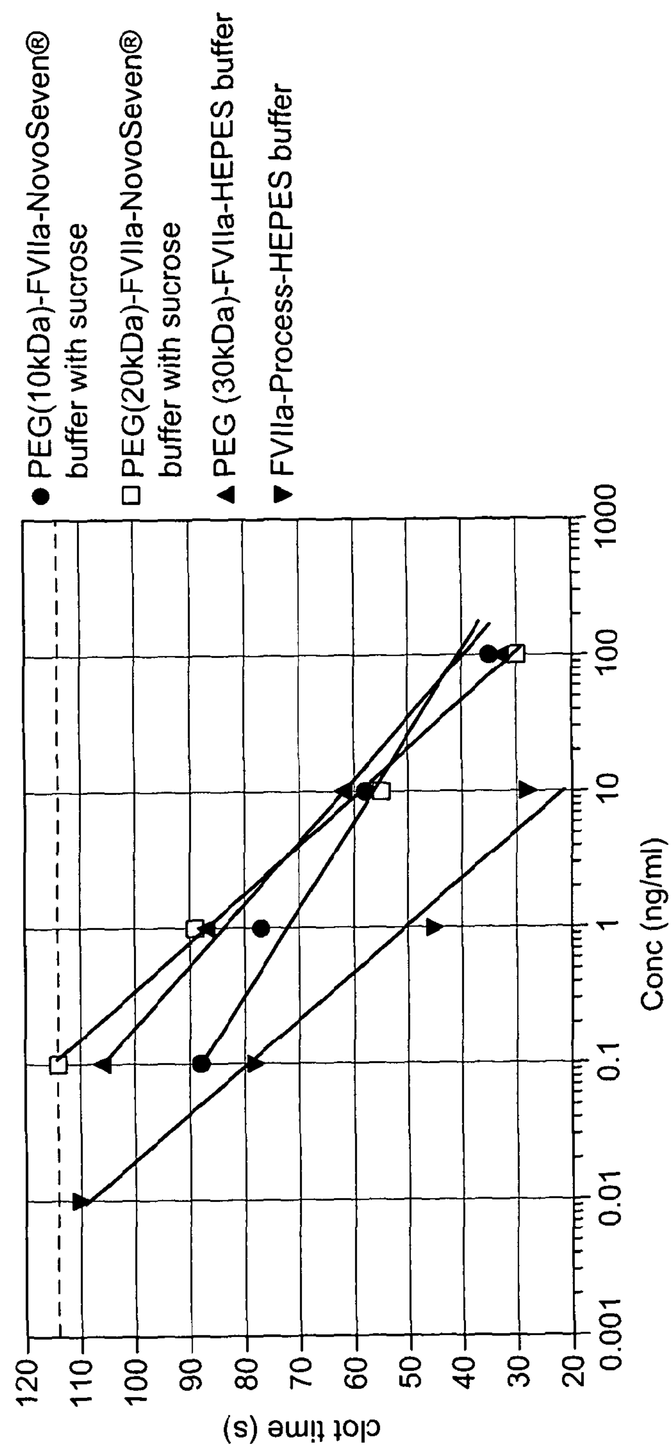

FIG. 9 shows concentration-dependent reduction in clotting times of PEGylated FVIIa (large-scale, lyophilised batch). Buffer (kit) clotted at 114 sec.

Figure 10:
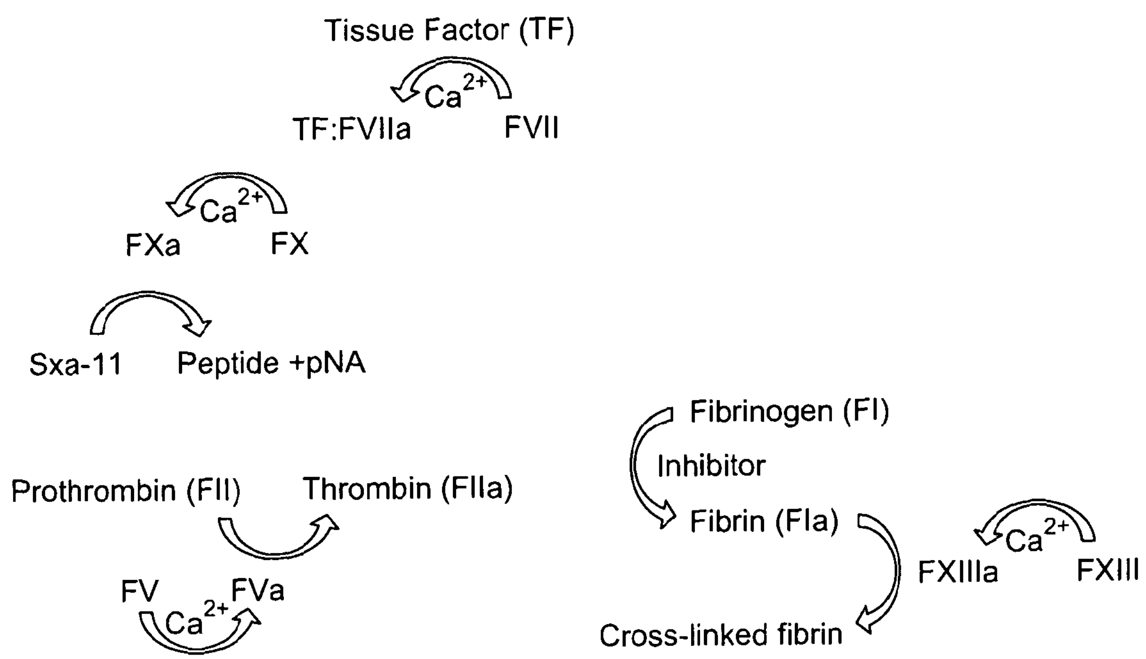

FIG. 10 shows a schematic diagram of the steps involved in a chromogenic assay. Arrows indicate thrombin-mediated amplification events and indicate an inhibitory effect.

Figure 11:
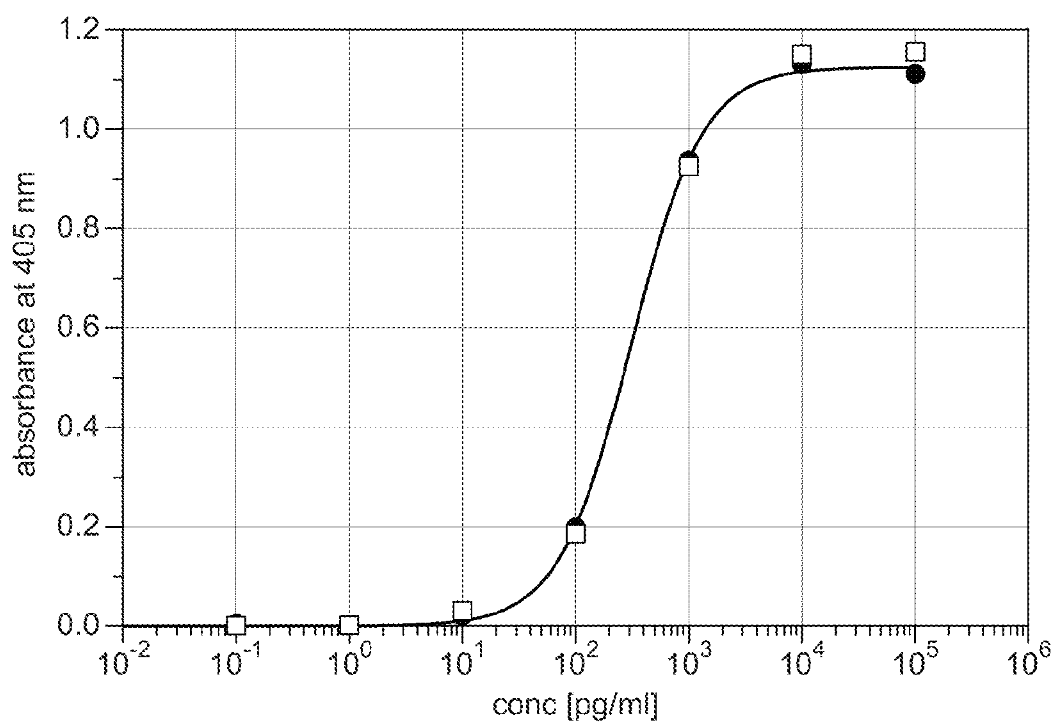

FIG. 11 shows representative results showing dose-dependent activities of FVIIa in HEPES buffer and FVIIa with 20 mM benzamidine.

Figure 12:
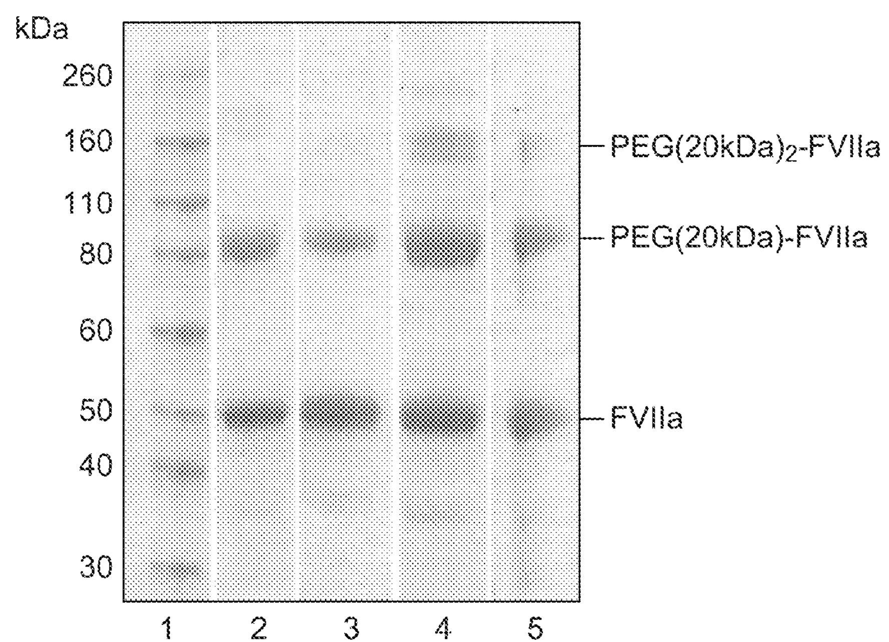
Figure 13A:
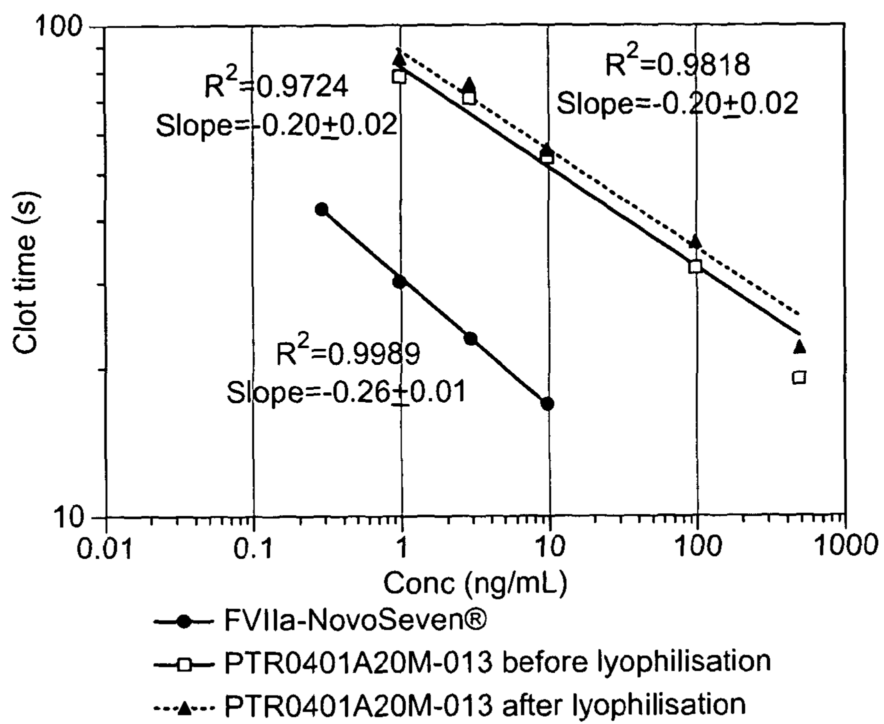
Figure 13B:
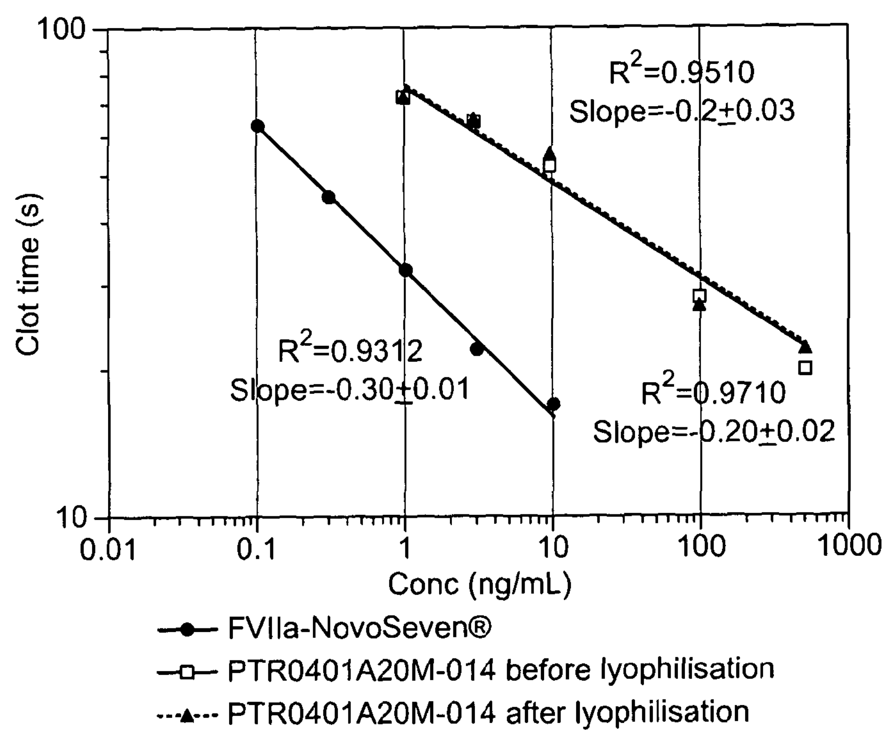
Figure 13C:
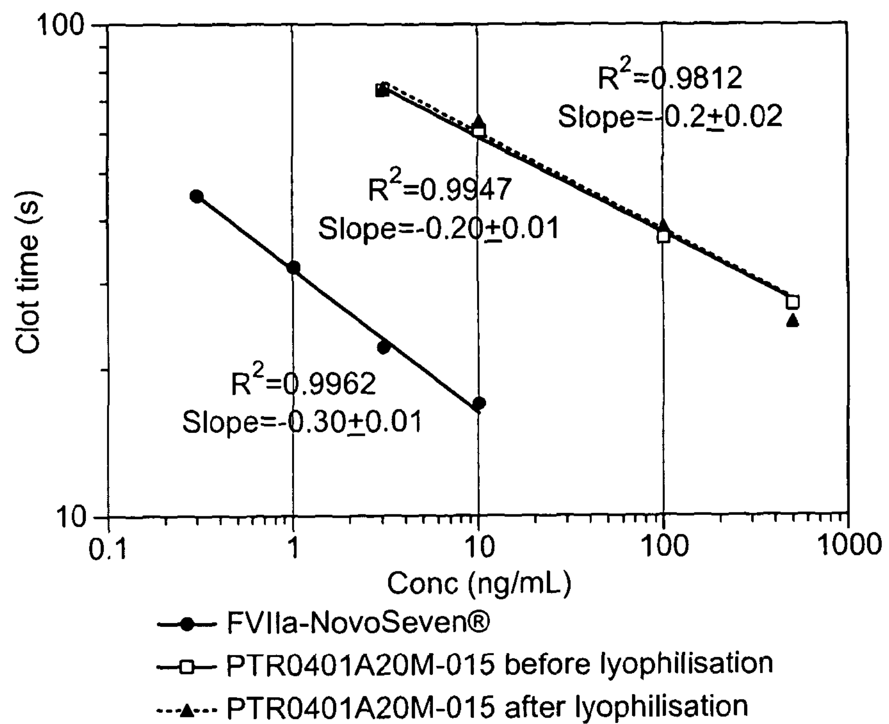
Figure 13D:
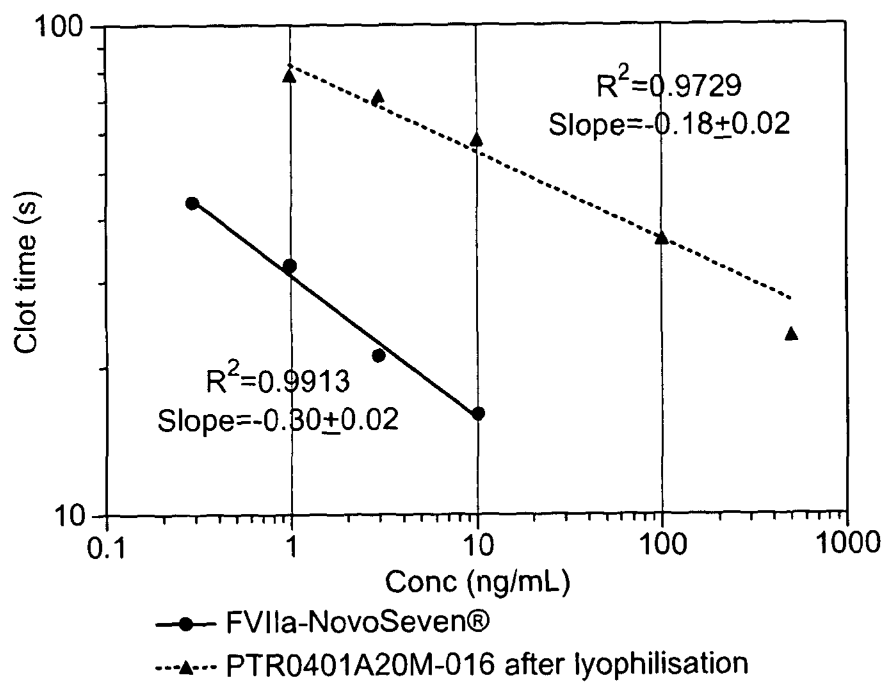

FIG. 12 shows SDS-PAGE analysis of TheraPEG™ PEGylation of FVIIa reaction mixtures. Lane 1 Novex® molecular weight markers; Lane 2-5, Reaction mixtures for PEG(20 kDa)-FVIIa batches 2 mg FVIIa, 3 mg FVIIa, (2 mg FVIIa & 3 mg FVIIa respectively.

FIG. 13 shows concentration-dependent decrease in clotting times of PEGylated FVIIa produced for rat PK study (4 batches a-d).

Figure 14:
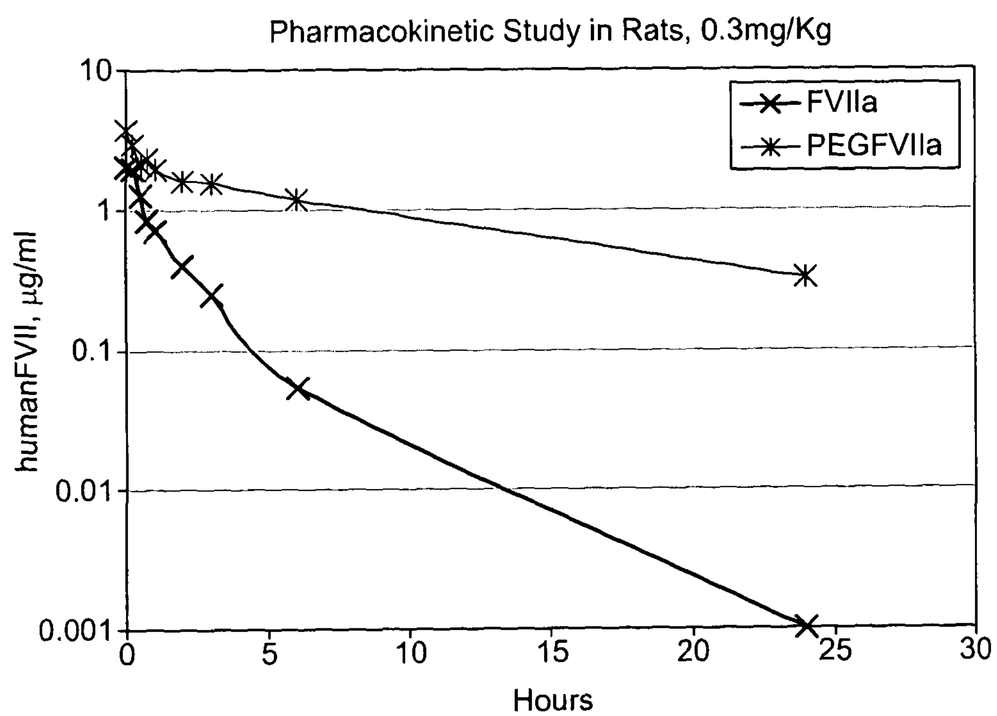

FIG. 14 shows the pharmacokinetic profiles of FVIIa and PEGFVIIa as measured ex-vivo by ELISA in terms of concentration of human FVIIa (μg/ml) measured with respect to time (hours).

Figure 15:
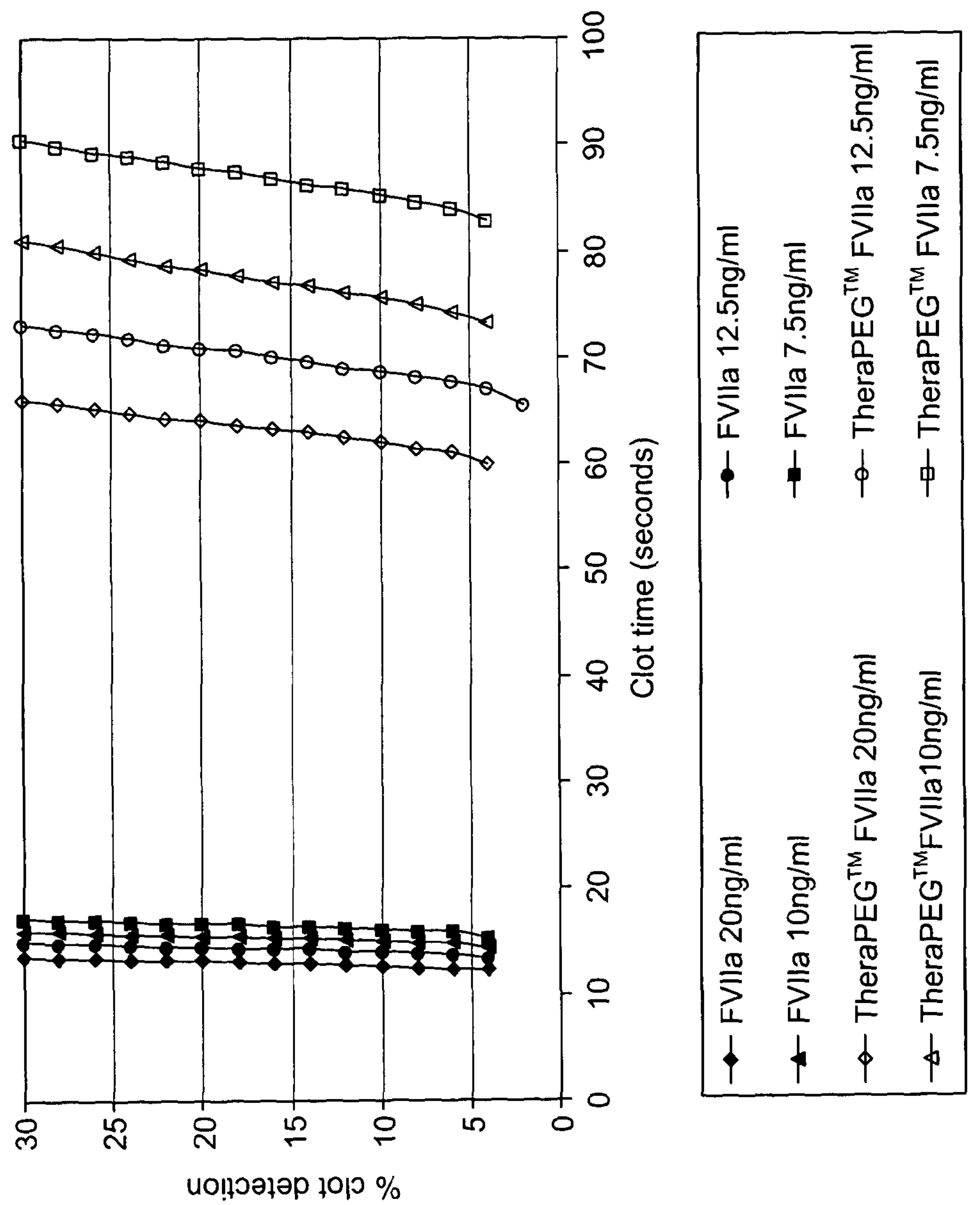

FIG. 15 shows a comparison of Rate of Clotting Reaction for FVIIa and PEGylated FVIIa.

Figure 16:
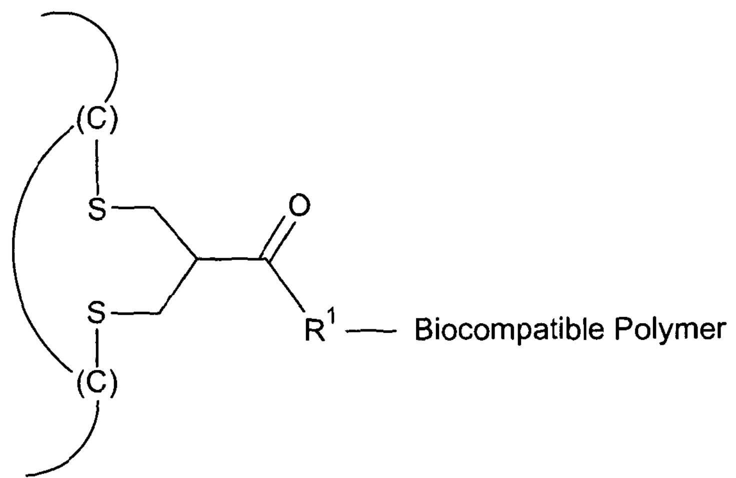
Figure 16:
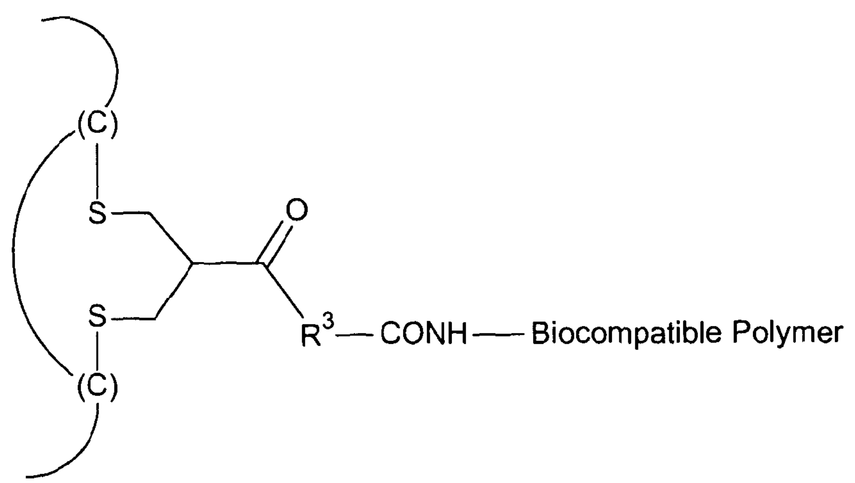

FIG. 16 shows two alternative schematic structures of conjugates of the invention in which FVIIa is represented by a black curved line, (C) represents a cysteine residue of FVIIa and where FVIIa is shown conjugated to a biocompatible polymer by a linker as described herein.

The invention will now be described further with reference to the following Examples which are present for the purposes of illustration only.

EXAMPLE 1

Disulphide PEGylation of FVIIa

Disulphide PEGylation of recombinant human FVIIa (NovoSeven®) was carried out according to a modified version of the procedure described by Shaunak et al. in *Nat Chem. Biol.* 2006; 2(6):312-313 and in Brocchini et al in *Nature Protocols,* 2006; 1(5): 2241-2252.

EXAMPLE 2

Disulphide Bond Reduction

Figure 1:
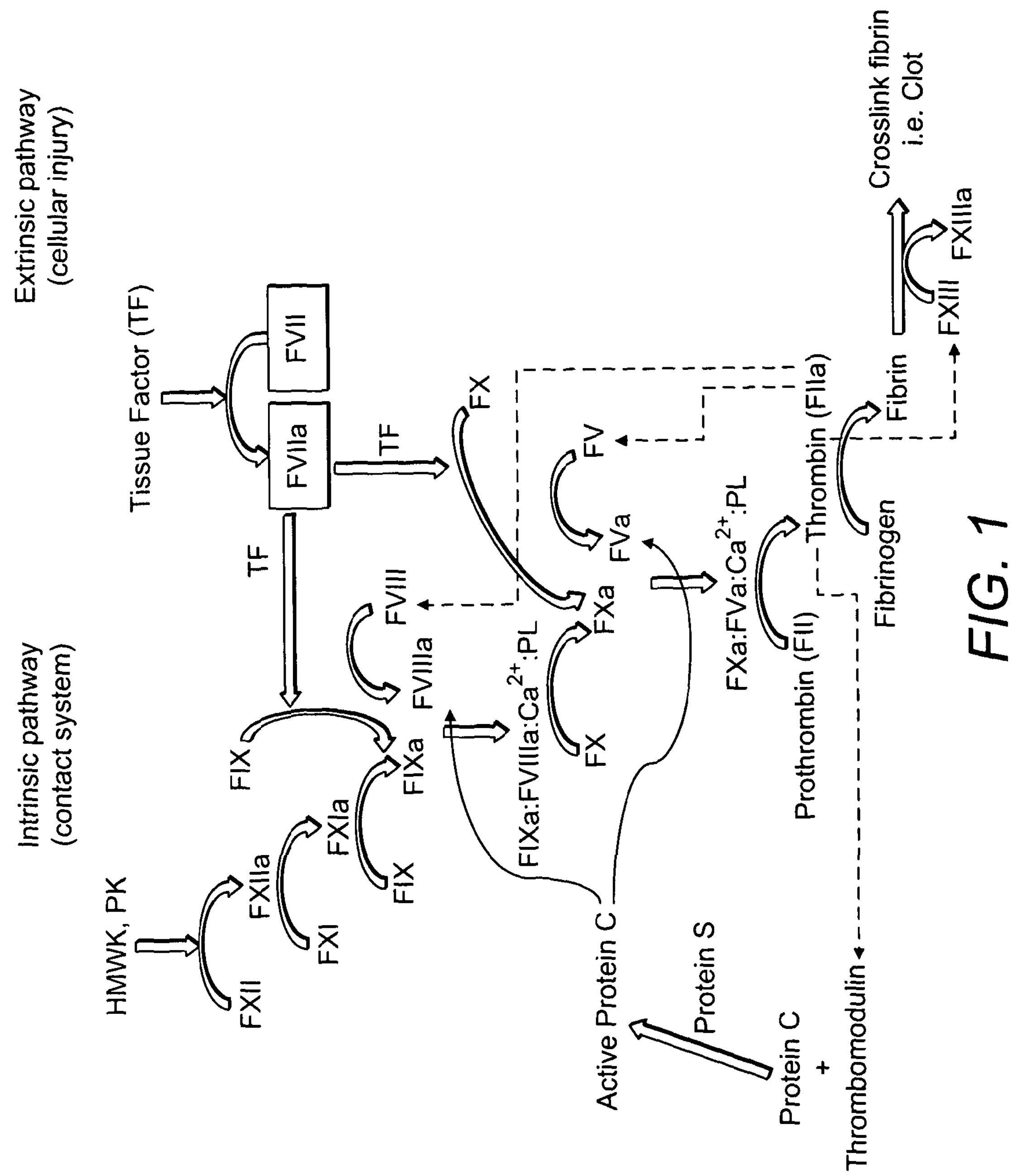
Figure 2:
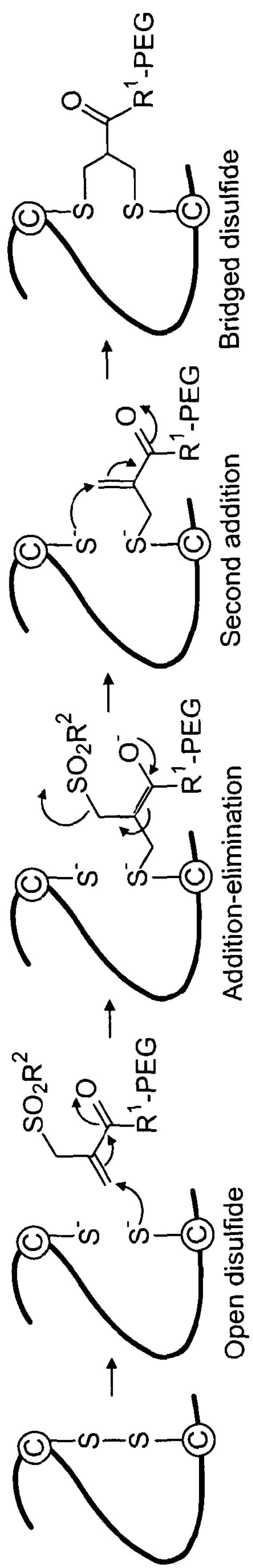
FIG. 2 shows the steps involved in disulphide-specific biopolymer conjugation chemistry with the use of a PEGylation reagent as an example of a conjugation reagent (from Shaunak et al. in *Nat Chem. Biol.* 2006; 2(6):312-313).
Figure 3A:
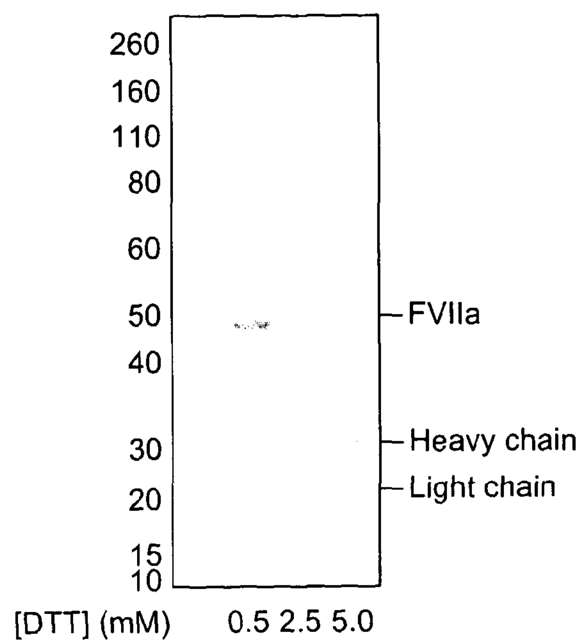
FIG. 3 shows SDS-PAGE showing FVIIa after reduction with DTT (panel A) or TCEP/SeCys (panel B).
Figure 3B:
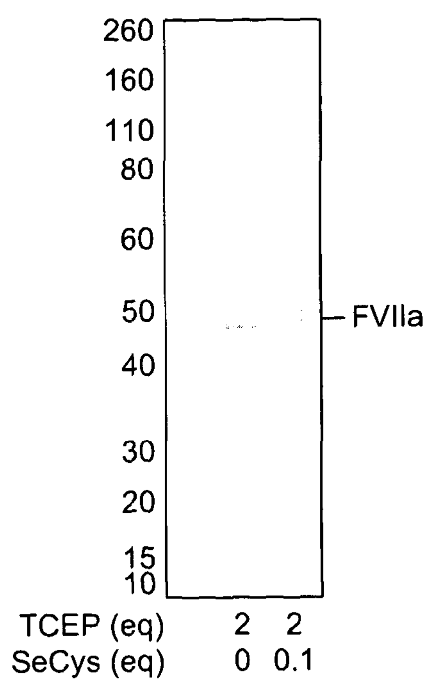

The TheraPEG™ PEGylation process requires reduction of disulphide bonds. Since FVIIa is a heterodimer formed of heavy and light chains joined by a single disulphide, an initial investigation of reduction conditions was carried out to determine whether reduction could be carried out without cleavage of the interchain disulphide. It was found that reduction with DTT in the range 0.5-5 mM resulted in reduction of the interchain disulphide yielding heavy and light chain (FIG. 3A). However, use of a light molar excess or the reducing agent tris(2-carboxyethyl)phosphine (TCEP), either in the presence or absence of selenocystamine (SeCys), resulted in little or no cleavage of the interchain disulphide (FIG. 3B). The presence of reduced intrachain disulphides under these conditions was confirmed by the addition of PEG reagent that reacted with the cysteine thiols to yield PEGylated species.

EXAMPLE 3

PEGylation of FVIIa

Initial assessment of the use of TheraPEG™ for PEGylation of FVIIa was carried out in small scale reactions (10-20 μg FVIIa). This allowed identification of conditions that could be used to reproducibly prepare mono-PEGylated FVIIa using 2 molar equivalents of PEG reagent. The effect of adding benzamidine to prevent proteolysis was investigated in early experiments. It was found that this had no effect on the PEGylation based on SDS-PAGE analysis and was therefore added to all subsequent reactions.

Reactions were scaled up (0.2-0.3 mg FVIIa) to produce PEGylated FVIIa for initial in vitro assessment. Samples of PEG(20 kDa)-FVIIa and one sample of PEG(10 kDa)-FVIIa were produced for in vitro analysis (see Table 1). It was found that increasing the temperature of the PEGylation reactions increased the conversion of FVIIa to PEG-FVIIa as approximated by integration of peaks in the chromatogram for heparin affinity purification. However, initial in vitro assessment indicated that the increase in temperature may have a negative effect on the activity of the PEGylated product and therefore subsequent reactions were carried out at lower temperatures (see Example 5).

TABLE 1

| Initial PEGylation Reactions | | |
|---|---|---|
| PEG Size (kDa) | Reaction Temperature (° C.) | Conversion (%) |
| 20 | 4 | 43 |
| 20 | 20 | 80 |
| 20 | 20 | 72 |
| 20 | 4 | 40 |
| 20 | 4 | 22 |
| 20 | 20 for 1 h then 4 | 40 |
| 10 | 20 for 1 h then 4 | 25 |

Various purification conditions were investigated for isolation of the PEGylated material. The first sample of PEG(20 kDa)-FVIIa was purified by heparin affinity and the second sample by heparin affinity followed by DEAE anion exchange. Benzamidine was not included in the buffers for purification of these batches. For all other batches, purification was carried out by heparin affinity with benzamidine in the buffers, followed by size exclusion chromatography (SEC). Benzamidine was initially included in buffers for SEC but it made identification of the peaks difficult due to very strong absorbance at 280 nm. Therefore, benzamidine was removed from the SEC buffers but added to samples immediately after elution.

To generate material for in vitro assessment, reactions were scaled up further to 1 mg FVIIa. Using conditions determined in smaller scale reactions 10 kDa, 20 kDa and 30 kDa PEGylated variants of FVIIa were prepared (FIG. 4).

After purification by heparin affinity chromatography followed by SEC as described above, PEGylated products were analysed by SDS-PAGE to demonstrate purity (FIG. 5) and quantified by BCA assay.

EXAMPLE 4

Evaluation of In Vitro Activity of PEGylated FVIIa by PT Assay

The activity of FVIIa and PEGylated FVIIa was determined using a modified prothrombin time (PT) assay (STA-CLOT VIIa-rTF, Diagnostica Stago, Paris, catalogue no. 00281). The recombinant soluble tissue factor (rsTF) supplied in the kit is specific for FVIIa. Calcium chloride required for clotting is not supplied in the kit, therefore 25 mM calcium chloride (Diagnostica Stago, catalogue no. 00367) was purchased for use in the assay. FIG. 6 shows the components provided and the steps involved in the assay (orange) within the coagulation cascade.

All assays were performed using a manual coagulation method. FVIIa or PEGylated FVIIa (50 μL) was pipetted into the reaction vessel (glass vial with plastic cap). FVII deficient plasma (50 μL) was then added into the reaction vessel followed by 50 μL of rsTF and then phospholipid was added into the reaction tube and it was incubated for 180 s at 37° C. After this time, 50 μL of 25 mM calcium chloride (pre-warmed to 37° C.) was added to the reaction mixture whilst simultaneously starting a timer. The reaction tube was gently rocked back and forth in the 37° C. water bath and careful observation was carried out to determine the formation of a clot. Immediately upon formation of the fibrin clot, the clot time was recorded.

The suitable concentration range for determining FVIIa activity in this assay has been established to be between 0.01-10 ng/mL and the concentration range for PEGylated FVIIa has been established to be between 0.10-100 ng/mL. The initial concentration of PEGylated FVIIa used in assays was therefore an order of magnitude lower than FVIIa in the PT assay due to the fast clotting time observed for the unP- EGylated protein, for which a concentration of 100 ng/mL would result in immediate clotting.

EXAMPLE 5

Evaluation of PEGylated FVIIa Activity by PT Assay

Initial assessment of PEGylated FVIIa was carried out with samples yielded from PEGylation reactions which started with 0.2-0.3 mg FVIIa. Samples of both 10 kDa PEGylated FVIIa and 20 kDa PEGylated FVIIa were tested. The first experiments carried out were with batches of PEG(20 kDa)-FVIIa which were supplied in citrate buffer and showed poor activity. Subsequent samples were supplied in HEPES buffer. The results of PT assays for batches supplied in HEPES buffer are listed in Table 2. The benzamidine concentration was 4 mM in these samples of PEG-FVIIa after dilution to the highest concentration of FVIIa tested (100 ng/mL).

TABLE 2

Clot Times for Samples of PEGylated FVIIa at 100 ng/ml (HEPES Buffer)

| PEG Size (kD) | Clot Time (100 ng/ml) | FVIIa Clot Time (10 ng/ml) | Buffer Clot Time |
|---|---|---|---|
| 20 | 100 s | 48 s | 114 s |
| 20 | 99 s | 48 s | 114 s |
| 20 | 75 s | 48 s | 114 s |
| 20 | 90 s | 48 s | 114 s |
| 20 | 67 s | 48 s | 114 s |
| 10 | 65 s | 48 s | 114 s |

The concentration-dependent change in clot time for 20 kDa and 10 kDa PEGylated FVIIa was investigated over a concentration range of 0.1-100 ng/mL (FIG. 7). These samples showed a similar change in clot times with increasing concentration as in the earlier investigation. Since the curves for different PEG sizes are parallel, any changes in clotting time as compared to the FVIIa in HEPES buffer is likely to be due to PEGylation. Based on the lines of best fit, the activity range of the 10 kDa and 20 kDa PEGylated FVIIa was 1.3%-2.5%.

Samples of 10 kDa and 20 kDa PEGylated FVIIa from larger scale reactions (1 mg FVIIa) were then tested. Clot times for these PEGylated samples were all comparable with each other and faster than observed for samples from smaller scale reactions (Table 3). The PEGylated samples for these reactions were supplied in a greater concentration and therefore required more dilution to reach the concentration of 100 ng/mL used as the highest concentration in the PT assay. The concentration-dependent change in clot time for these samples was compared with that for FVIIa (FIG. 8). A percentage activity range was calculated for these samples from lines of best fit and was found to be between 5 and 7.5%.

Aliquots of samples from larger scale 10 kDa and 20 kDa PEGylated FVIIa samples were buffer exchanged to include the excipients found in NovoSeven® (sucrose replaced mannitol as this was unavailable) and then lyophilised. The resulting powders were resuspended in water and analysed using the PT assay (FIG. 9). At the same time, the following samples were analysed: (1) a sample of PEG(30 kDa)-FVIIa prepared from a 1 mg scale reaction, (2) FVIIa which had gone through the PEGylation process but without having PEG added.

FVIIa which had been processed in a similar way to PEGylated FVIIa but did not have PEG added showed similar changes in clotting time as compared to FVIIa which had been buffered exchanged in HEPES buffer (FIG. 8). This indicates that any reduction in activity observed is due to the attachment of PEG and not to the process. The 30 kDa PEGylated variant of FVIIa also exhibited similar activity to variants with smaller PEG size. Lyophilisation of 10 kDa and 20 kDa PEGylated FVIIa did not seem to affect activity at higher concentrations. At lower concentrations the lyophilised 10 kDa PEGylated variant seemed to exhibit activity similar to unPEGylated FVIIa. However, care should be taken when interpreting this value as this data is from a single experiment and repeat analysis is required to verify this result. Percentage activity ranges for these samples were determined from lines of best fit and are summarised in Table 3.

TABLE 3

Results from PT Assay using PEGylated Samples from Larger Scale Reactions

| PEG Size (kD) | Clot Time (100 ng/ml) | Activity % |
|---|---|---|
| 30 | 33 s | 5-7.7 |
| 20 | 36 s | 5-7.5 |
| 20 | 30 s | 5-9 |
| 10 | 34 s | 5-7.5 |
| 10 | 35 s | 7.7-33 |

EXAMPLE 6

Chromogenic Assay

The chromogenic assay (Hyphen Biomed, catalogue no. 221304) measures the activity of FVIIa by formation of a coloured substrate, and does not involve clot formation. This is achieved by activation of FX to FXa by FVIIa in the presence of calcium and thromoboplastin. FXa cleaves a chromogenic substrate, specific for FXa. This allows quantitative measurement of FVIIa (FIG. 10).

The assay was performed in a 96-well microtitre plate. All pre-warm and incubation steps were performed at 37° C. The sample (30 μL) was added to the microtitre plate and pre-warmed at 37° C. for 2 min. Pre-warmed R2 reagent (30 μL) was added to each well followed by pre-warmed R1 (60 μL) and these were mixed and incubated for 7 min. Chromogenic substrate (R3, pre-warmed) was then added at 60 μL per well and incubated for 5 min. The reaction was stopped by the addition of 60 μL of 20% acetic acid and absorbance was read at 405 nm.

Results from the chromogenic assay have shown that FVIIa in HEPES buffer is compatible with the assay and this gave a similar result to FVIIa with 20 mM benzamidine. An example of the results of a chromogenic assay is shown in FIG. 11. The ED50 values for FVIIa in HEPES buffer with 20 mM benzamidine is 307.6±9.0 pg/mL (15.4±0.5 mU/mL) and for FVIIa with 20 mM benzamidine it is 351.4±10.8 pg/mL (17.6±0.5 mU/mL).

The chromogenic assay range for FVIIa has been established between concentrations of 0.10 pg/mL-100 ng/mL. A concentration of PEGylated FVIIa in the milligrams range is required for the chromogenic assay. This is not feasible and therefore the chromogenic assay has not been used for PEGylated samples.

EXAMPLE 7

Production of 20 kD TheraPEG™-FVIIa for Rat PK study

The scale of PEGylation reactions was increased from 1 mg to 2-3 mg FVIIa. Production of 20 kDa TheraPEG™

FVIIa for a rat PK study was carried out in four sub-lots containing either 2 mg or 3 mg FVIIa (NovoSeven®). PEGylation was performed using conditions identified previously and purification was performed using heparin affinity chromatography to remove unreacted PEG reagent, followed by SEC to remove any remaining residual unPEGylated FVIIa and diPEGylated protein. Fractions containing monoPEGylated PEG(20 kDa)-FVIIa were pooled and buffer exchanged into NovoSeven® RT buffer constituents before lyophilisation.

Formation of a monoPEGylated product was confirmed for each PEGylation reaction by SDS-PAGE analysis (FIG. 12). The average percentage conversion of FVIIa to PEGylated FVIIa was 44.5±7.5% as approximated by integration of peaks in the chromatogram for heparin affinity purification. The final yield of PEGylated FVIIa was 1.09 mg of PEG(20 kDa)-FVIIa as determined by a Bradford total protein assay. This amount represented an average yield of 11.2±3.8%.

The in-vitro activity of PEG(20 kDa)-FVIIa was determined using the modified prothrombin time (PT) assay The analysis of clotting time during earlier studies (Example 5) was undertaken by plotting the data on a semi-log graph but this was changed to a log-log graph for the current study (FIG. 13) as this is the method recommended by the kit manufacturer. Percentage retained activity was calculated for samples pre and post lyophilisation. The average clot time (at 100 ng/ml) and retained activities of PEG(20 kDa)-FVIIa pre-lyophilisation were 33.0±4.5 s and 0.6±0.4%, respectively. The average clot time (at 100 ng/ml) and retained activities of PEG(20 kDa)-FVIIa post-lyophilisation were 34.8±4.7 s and 0.8±0.4%, respectively.

Differences were seen in the retained activity between the batches prepared for the rat study and batches prepared during the initial feasibility study (Examples 3-5). When the data for the initial feasibility study was reviewed it was found that the FVIIa standard gave longer clotting times at equivalent concentrations than the standards used for analysis of the rat study batches. The FVIIa standard used for analysis of the feasibility batches had been stored in non-siliconised microcentrifuge tubes for 15 days. Since this experiment was carried out it has become apparent that storage of FVIIa under these conditions may result in some protein sticking to the tube. Hence, when this standard was used the actual FVIIa concentration may have been lower than expected resulting in less being added to the assay than calculated. This would lead to longer clotting times and therefore lower apparent activity of the standard and consequently the percentage retained activity of the PEG(20 kDa)-FVIIa appeared higher. For the rat PK study, FVIIa standards were frozen at −80° C. in Eppendorf LoBind® tubes immediately after reconstitution which should prevent the FVIIa from adhering to the tube during storage and therefore give a more accurate result in the PT assay.

EXAMPLE 8

Pharmacokinetics of 20 KD TheraPEG™-FVIIa Versus NovoSeven® in Rats

The pharmacokinetic properties of PEG(20 kDa)-FVIIa was evaluated in male Sprague Dawley rats and compared directly to the pharmacokinetics of FVIIa (NovoSeven®) in this model. Nine animals per group were dosed by IV bolus in the tail vein at 0.3 mg/kg at a volume of 2.5 ml/kg. Blood samples were taken at 0.033, 0.25, 0.5, 0.75, 1.0, 2.0, 3.0, 6.0 and 24 hours. Plasma samples were prepared and FVIIa concentration analysed by ELISA. FIG. 14 shows a plot of time versus FVIIa concentration. The alpha, beta and overall plasma half-lives were calculated and are presented in Table 4. The results show that the plasma half life of TheraPEG™ (20 kDa)-FVIIa was significantly longer than that of FVIIa.

TABLE 4

Rat PK Study Results

| | Time (Hours) | |
|---|---|---|
| | PEG(20 kDa) - FVIIa | NovoSeven ® |
| Alpha t½ | 1.06 | 0.56 |
| Beta t½ | 8.91 | 3.71 |
| t½ | 6.81 | 3.01 |

EXAMPLE 9

Production of 20 KD TheraPEG™-FVIIa for Dog PK Study

The scale of PEGylation reactions was increased from 3 mg to 25 mg FVIIa via intermediate reactions performed at 5 and 10 mg scale. Production of PEG(20 kDa)-FVIIa for a dog PK study was carried out using two sources of FVIIa.

Preparation of PEG(20 kDa)-FVIIa using the first source of FVIIa (NovoSeven®) was carried out in 5 lots by PEGylation of FVIIa at reaction scales between 10 and 25 mg. Reaction conditions were identical for each batch and analysis by SDS-PAGE showed that the PEGylation was consistent. The average percentage conversion of FVIIa to PEGylated FVIIa was 41.8±11.7% as approximated by integration of peaks in the chromatogram for heparin affinity purification. The total final yield of PEGylated FVIIa was 15.3 mg of PEG(20 kDa)-FVIIa as determined by a Bradford total protein assay. This amount represented an average yield of 14.7±3.6%.

The in-vitro activity was calculated for samples pre and post lyophilisation. The average clot time (at 100 ng/ml) and retained activities cf. FVIIa of PEG(20 kDa)-FVIIa pre-lyophilisation were 28.5±3.5 s and 1.8±0.6%, respectively. The average clot time (at 100 ng/ml) and retained activities of PEG(20 kDa)-FVIIa cf. FVIIa post-lyophilisation were 32.2±4.1 s and 2.2±2.5%, respectively.

Preparation of PEG(20 kDa)-FVIIa using the second source of FVIIa was carried out in 3 lots by PEGylation of FVIIa at 25 mg reaction scales. Reaction conditions were identical for each batch and analysis by SDS-PAGE showed that the PEGylation was consistent. The average percentage conversion of FVIIa to PEGylated FVIIa was 40.3±2.9% as approximated by integration of peaks in the chromatogram for heparin affinity purification. The total final yield of PEGylated FVIIa was 13.1 mg of PEG(20 kDa)-FVIIa as determined by a Bradford total protein assay. This amount represented an average yield of 17.5±6.9%.

The in-vitro activity was calculated for samples pre and post lyophilisation. The average clot time (at 100 ng/ml) and retained activities of PEG(20 kDa)-FVIIa cf. FVIIa pre-lyophilisation were 37.0±3.5 s and 1.5±0.6%, respectively. The average clot time (at 100 ng/ml) and retained activities of PEG(20 kDa)-FVIIa cf. FVIIa post-lyophilisation were 35.7±1.1 s and 1.3±0.3% respectively.

EXAMPLE 10

In-Vitro Analysis of PEG(20 kDa)-FVIIa by Measurement of Rate of Clotting Reaction In order to establish whether PEG(20 kDa)-FVIIa clots at the same rate as FVIIa, the modified PT assay was performed on a Sysmex CA50 coagulation analyser. As a clot forms, the analyser records the change in scattered light from 2-80%. By plotting the clotting time against the % clot detection, the rate of clotting can be calculated from the slope of the curve and can be compared between samples. It is important to compare samples at the same concentrations since there is a concentration dependant effect on the reaction rate.

The rate of reaction of FVIIa and PEG(20 kDa)-FVIIa was measured at four different concentrations; 7.5, 10, 12.5 and 20 ng/ml. (FIG. 15). The mean rate of reaction of PEGylated FVIIa was found to be 22% of that of FVIIa across the four concentrations tested (Table 5).

TABLE 5

Rate of Reaction of PEGylated FVIIa vs FVIIa

| Concentration | Rate of Reaction (% clot/sec) | | PEGylated FVIIa |
|---|---|---|---|
| (ng/ml) | FVIIa | PEGylated FVIIa | % Activity cf. FVIIa |
| 7.5 | 15.838 | 3.6436 | 23.0 |
| 10 | 17.937 | 3.5308 | 19.7 |
| 12.5 | 17.414 | 4.0073 | 23.0 |
| 20 | 20.235 | 4.6423 | 22.9 |
| | | Mean | 22.2 |

EXAMPLE 11

Pharmacokinetics and Blood Clotting of 20 KD TheraPEG™-FVIIa Products in Haemophilia A Dogs The objective of this study is to determine if the two different PEG(20 kDa)-FVIIa products (Example 9) had favourable pharmacological profiles and were efficacious in inhibitor prone haemophilia A dogs compared to NovoSeven® and another source of FVIIa. These two PEGylated products differ in the source of FVIIa used in their preparation.

Pretreatment CBC, serum chemistry profile fibrinogen, FDPs, thrombin time (TT) and UA are performed on each dog to verify normal health status and for baseline comparison. Additional serum and plasma aliquots are frozen at −70 C for future clotting factor and inhibitor antibody assays. One dog is employed per test article initially, with the plan to extend testing if biological half-life and safety prove satisfactory.

Doses of each test article are selected to give equipotent dosing as based on the in vitro rate reaction assay (Example 10) and dosing is achieved by IV infusion into the cephalic vein.

Plasma samples are obtained at 30 minutes, 1, 2, 4, 8, 16, 24, 36, 48, 72, 96, and 120 hours by collection of blood into 0.109M trisodium citrate anticoagulant, followed by centrifugation and freezing at −70 C. Plasma samples are tested for the following: aPTT, Staclot FVIIa activity, FVIIa antigen levels by ELISA and thromboelastogram clot quality. At the time of venipuncture the whole blood clotting time (WBCT) is performed immediately. The aPTT, Staclot assay and WBCT are used to estimate the biological half-life, whereas the FVIIa ELISA is used to determine the half-life based on protein antigen levels.

Unexpected toxicities are screened for by performing CBC and serum chemistry tests at 48 hours and 5 days following product administration. Fibrinogen, FDPs and thrombin time (TT) are evaluated to test for increased thrombosis risk. A Bethesda assay is used to screen for the presences of neutralising antibodies.

The invention claimed is:

1. A Factor VIIa-polyethylene glycol conjugate, wherein one or more polyethylene glycol groups are conjugated to FVIIa by a linker group bridging the sulphur atoms of two cysteine residues that formed a disulphide bond in FVIIa, wherein each polyethylene glycol group conjugated to FVIIa by a linker group bridging the sulphur atoms of two cysteine residues that formed a disulphide bond in FVIIa:

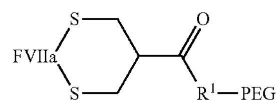

wherein $R^1$ is a substituent which is a direct bond, an alkylene group, or an optionally-substituted aryl or heteroaryl group; wherein the aryl group is selected from the group consisting of phenyl, benzoyl and naphthyl; wherein a suitable heteroaryl group is selected from the group consisting of pyridine, pyrrole, furan, pyran, imidazole, pyrazole, oxazole, pyridazine, pyrimidine and purine; wherein linkage to the polymer is by a hydrolytically labile bond, or by a nonlabile bond.

2. The Factor VIIa-polyethylene glycol conjugate of claim 1 wherein the polyethylene glycol has a molecular weight of about 5-100 kDa.

3. The Factor VIIa-polyethylene glycol conjugate of claim 1, wherein alkylene group is a $C_{1-10}$ alkylene group.

4. A pharmaceutical composition comprising the Factor VIIa-polyethylene glycol conjugate of claim 1.

5. The pharmaceutical composition of claim 4 further comprising a pharmaceutically acceptable diluent, adjuvant or carrier.

6. The pharmaceutical composition of claim 4 further comprising another pharmaceutically active agent.

7. The pharmaceutical composition of claim 4, wherein the composition is suitable for parenteral administration.

8. The pharmaceutical composition of claim 4, wherein the composition is suitable for intradermal, subcutaneous, and intramuscular injections, and intravenous or intraosseous infusions.

9. The pharmaceutical composition of claim 4 wherein the composition is in the form of a solution, suspension or emulsion.

10. The pharmaceutical composition of claim 4, wherein the FVIIa conjugate has a longer half-life as compared to unmodified FVIIa.

11. The pharmaceutical composition of claim 4, wherein the FVIIa conjugate has a higher AUC as compared to unmodified FVIIa.

12. The pharmaceutical composition of claim 4, wherein the FVIIa conjugate has a higher bioavailability as compared to unmodified FVIIa.

13. The pharmaceutical composition of claim 4, wherein the FVIIa conjugate has a lower immunogenicity as compared to unmodified FVIIa.

14. A method of treatment of a blood clotting disease or trauma comprising administration of the pharmaceutical composition of claim 4 to a patient in need thereof.

15. The method of treatment as claimed in claim 14 wherein the blood clotting disease is haemophilia A or haemophilia B.

16. A method to reduce the risk of hemarthrosis, hemorrhage, gastrointestinal bleeding and menorrhagia in a patient with haemophilia A, haemophilia B or trauma, comprising administering to a patient in need thereof a pharmaceutical composition comprising the FVIIa conjugate of claim 4.

17. The method of claim 16, wherein the composition is administered subcutaneously.

18. The method of claim 16, wherein the composition is administered intravenously.

19. The method of claim 16, wherein the composition is administered once every one to fourteen days.

20. A method of treatment of a blood clotting disease or trauma comprising administration of the pharmaceutical composition of claim 4 to a mammal in need thereof.

21. The method of treatment as claimed in claim 20 wherein the blood clotting disease is haemophilia A or haemophilia B.

22. A method to reduce the risk of hemarthrosis, hemorrhage, gastrointestinal bleeding and menorrhagia in a mammal with haemophilia A, haemophilia B or trauma, comprising administering to a mammal in need thereof a pharmaceutical composition comprising the FVIIa conjugate of claim 4.

23. The method of claim 22, wherein the composition is administered subcutaneously.

24. The method of claim 22, wherein the composition is administered intravenously.

25. The method of claim 22, wherein the composition is administered once every one to fourteen days.

* * * * *